United States Patent [19]

Fukushima et al.

[11] Patent Number: 5,665,270
[45] Date of Patent: Sep. 9, 1997

[54] OPTICALLY ACTIVE TRIFLUOROLACTIC ACID DERIVATIVE AND LIQUID CRYSTAL COMPOSITION

[75] Inventors: Masatoshi Fukushima; Shinichi Saito, both of Chiba-ken, Japan

[73] Assignee: Chisso Corporation, Ohsaka-fu, Japan

[21] Appl. No.: 142,292

[22] PCT Filed: May 20, 1992

[86] PCT No.: PCT/JP92/00646

§ 371 Date: May 4, 1994

§ 102(e) Date: May 4, 1994

[87] PCT Pub. No.: WO92/20641

PCT Pub. Date: Nov. 26, 1992

[30] Foreign Application Priority Data

May 20, 1991 [JP] Japan .................. 3-114947
Aug. 23, 1991 [JP] Japan .................. 3-212312
Oct. 3, 1991 [JP] Japan .................. 3-256573

[51] Int. Cl.[6] .................. C09K 19/52; C07D 239/02; C07C 69/76; C07C 25/13
[52] U.S. Cl. .................. 252/299.01; 252/299.61; 252/299.63; 252/299.64; 252/299.65; 252/299.66; 252/299.67; 544/242; 544/336; 546/1; 548/136; 560/55; 560/76; 570/124; 570/127; 570/129
[58] Field of Search .................. 252/299.01, 299.61, 252/299.63, 299.64, 299.65, 299.66, 299.67; 544/242, 336; 546/1; 548/136; 560/55, 76; 570/124, 127, 129

[56] References Cited

U.S. PATENT DOCUMENTS 5,204,020 4/1993 Suzuki et al. .................. 252/299.67

FOREIGN PATENT DOCUMENTS 64-003154 1/1989 Japan .
64-3154 1/1989 Japan .
2-131444 5/1990 Japan .
02250840 10/1990 Japan .
2-250840 10/1990 Japan .

OTHER PUBLICATIONS

Caplus :431747 Abstract, 1989.
Caplus :101130 Abstract, 1991.
Haydock et al, "Analogues of clofibrate and clobuzarit containing floorine in the side chains" in Eur. J. Med. Chem.–Chem. Ther., 1984–19. pp. 205–214.
Journal of Organic chemistry, vol. 55, No. 13, perfrancesco Bravo et al "Synthesis of SC–β, β, β–Trifluorolactic acid and (S)–α–methoxy–α–trifluoromethyl–phenylacetic acid from (R)–methyl–p–Tolylsulfoxide", pp. 4216–4218. (1990).

Ponomarenko et al., "Nature Of Catalytic Centers In Polymerization Of Trifluoropropylene Oxide In The Presence Of Ferric Chloride", Chemical Abstracts, vol. 70, 1969, Abstract 97245q.

Primary Examiner—Shean C. Wu
Attorney, Agent, or Firm—Wenderoth, Lind & Ponack

[57] ABSTRACT

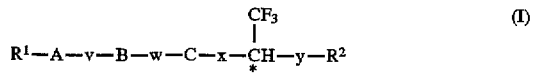

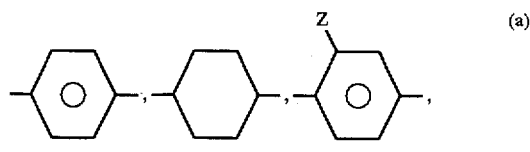

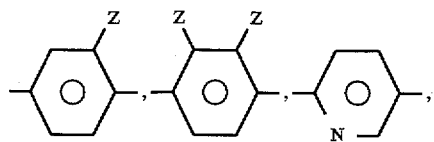

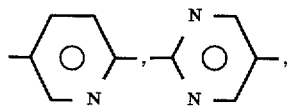

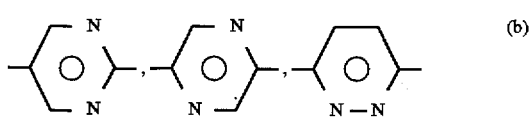

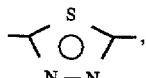

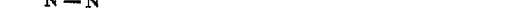 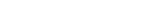

An optically active compound derived from a novel trifluorolactic acid, useful as a component of a ferroelectric liquid crystal composition, and a liquid crystal composition. A compound represented by general formula (I), wherein $R^1$ represents $C_1$ to $C_{18}$ alkyl, alkoxy, $C_2$ to $C_{18}$ alkanoyl, alkanoyloxy or alkoxycarbonyl; $R^2$ represents optionally alkoxy-substituted alkyl (where the total number of the carbon atoms is 1 to 15); A, B and C represent each independently the group (a) or (b); v and w represent each independently —COO—, —OCO—, —CH$_2$O—, —OCH$_2$—, —CH$_2$—CH$_2$—, —CH=CH—, —C≡C— or a single bond; and x and y together represent any of the following combinations: —COO— and —COO—; —COO— and —CO—; —COO— and —CH$_2$O—; —COO— and —CH$_2$OCO—; —COO— and —CH$_2$OCOO—; —O— and —CH$_2$O—; —O— and —CH$_2$OCO—; and —O— and —CH$_2$OCOO—.

9 Claims, 2 Drawing Sheets

1H-NMR CHART OF THE COMPOUND OF EXAMPLE 3

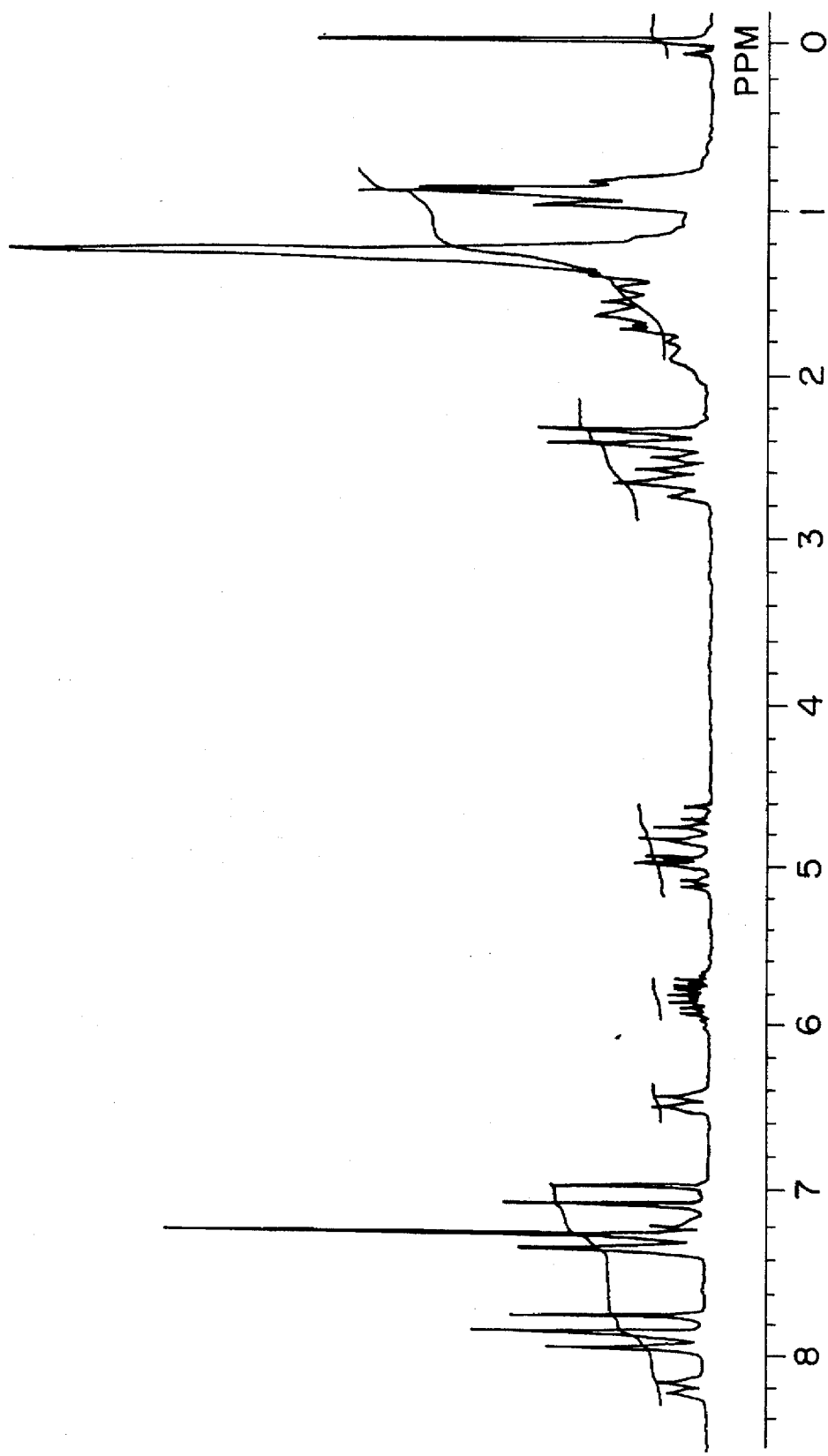

OPTICALLY ACTIVE TRIFLUOROLACTIC ACID DERIVATIVE AND LIQUID CRYSTAL COMPOSITION

This application is a 371 of PCT/JP92/00646 filed May 20, 1992.

FIELD OF THE ART

This invention relates to an optically active trifluorolactic acid derivative and a liquid crystal composition. More particularly it relates to a novel optically active compound derived from trifluorolactic acid and useful as a component of ferroelectric liquid crystal compositions. Further, it relates to a novel optically active intermediate derivable from optically active trifluorolactic acid in the preparation of the above optically active compounds.

BACKGROUND OF THE ART

At present, TN (twisted nematic) type display mode has been most broadly used. This TN display has many advantages such as low driving voltage, low power consumption, etc. However, it is far inferior in the aspect of response speed to emissive display elements such as cathode ray tube, electroluminescence, plasma display, etc. A new type TN display element having a twist angle increased up to 180° to 270° has also been developed, but it is still yet inferior in the aspect of response speed. Efforts for various improvements have been made as described above, and nevertheless, development of TN display element having a high response speed has not yet been realized.

However, as to a new display mode using a ferroelectric liquid crystal which has now been extensively researched, a notable improvement in the response speed has been anticipated (Clark et al, Applied Phys. lett., 36, 899 (1980)). This display mode utilizes chiral smectic phases exhibiting ferroelectricity such as chiral smectic C phase (hereinafter abbreviated to Sc* phase), etc.

A number of specific features have been required for ferroelectric liquid crystal materials having been used for ferroelectric liquid crystal display elements practically used. Representative items of the above specific features are spontaneous polarization (Ps), tilt angle (θ), viscosity (η), liquid crystal phase sequence, etc.

The molecule in the ferroelectric liquid crystals can move only on a cone, and it can form two states wherein the parallel direction of the molecule is perpendicular to the electric field corresponding to a direction of the electric field. The angle made between the two states is referred as cone angle and the half of the cone angle is referred to as tilt angle (θ).

The ferroelectric liquid crystal display mode currently includes mainly two modes i.e. a mode referred to as a birefringence mode wherein two upper and lower polarizers are used, and a mode referred to as guest-host mode (G.H.) wherein one polarizer is used and a dichroic dyestuff is added. In order that the ratio of brightness of the bright and dark states (contrast ratio) is the best, a tilt angle of 22.5° is required for the birefringence mode, while a tilt angle of 45° is required for the G.H. mode.

Further, since a relationship of τ∝η/Ps is existent among the responce time (τ), Ps and η, a material having a larger Ps and a lower η is required for making the response speed higher. A number of specific features are required for ferroelectric liquid crystal materials used for ferroelectric liquid crystal display elements practically used, as described above, but any single compound cannot satisfy the requirements in the current state. Hence the ferroelectric liquid crystal compositions have been provided in the form of a mixture of a numer of materials. The compositions may be composed of even either liquid crystal compounds or non-liquid crystalline compounds. Ferroelectric liquid crystal compositions can be prepared by composing only of ferroelectric liquid crystal compounds, or by a method of mixing as a basic substance, a compound or a composition exhibiting tilted smectic phases of achiral smectic C, F, G, H, I, etc. (hereinafter abbreviated to Sc phase etc.), with one member or more of ferroelectric liquid crystal compounds or non-liquid crystalline, optically active compounds to thereby form a composition exhibiting a ferroelectric liquid crystalline phase as a whole.

As such a basic substance, a group of compounds of various series exhibiting achiral smectic liquid crystal phases of Sc etc. have been used, but liquid crystal compounds or liquid crystal compositions exhibiting smectic phases within a broad temperature range of from low temperatures to room temperature or higher have been practically used. Sc phases among the smectic phases exhibit the highest speed response properties among the ferroelectric liquid crystal phases, hence the Sc phases broadly and generally constitute the liquid crystal phases of the basic substance. As the constituting components of these smectic C liquid crystal compositions, liquid crystal compounds such as those of phenyl benzoate group, Schiff's base group, biphenyl group, phenylpyridine group, phenylpyrimidine group, etc. are exemplified. Representative examples of these compounds are as follows wherein $R^8$ and $R^9$ each independently represent an alkyl group or alkoxy group of 1 to 20 carbon atoms:

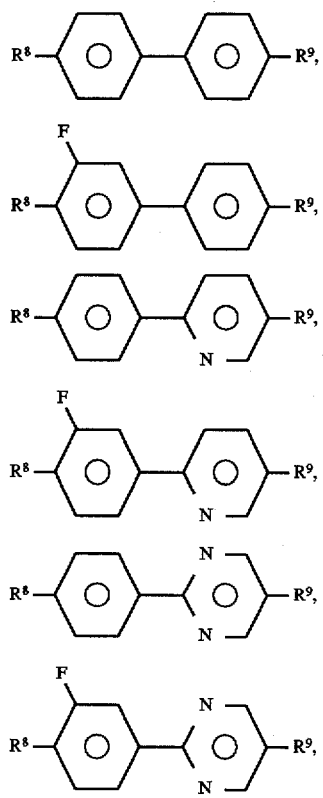

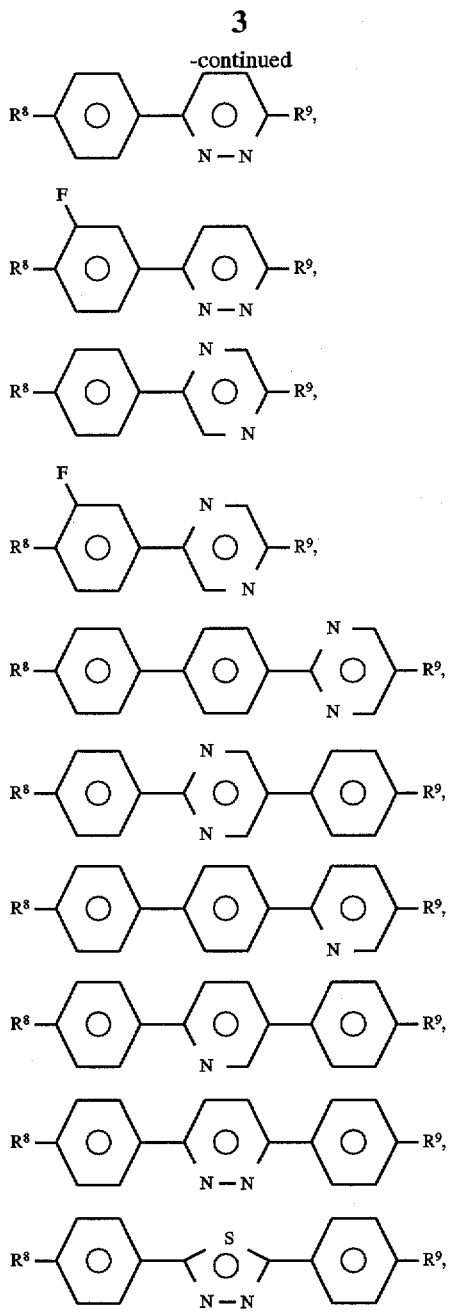

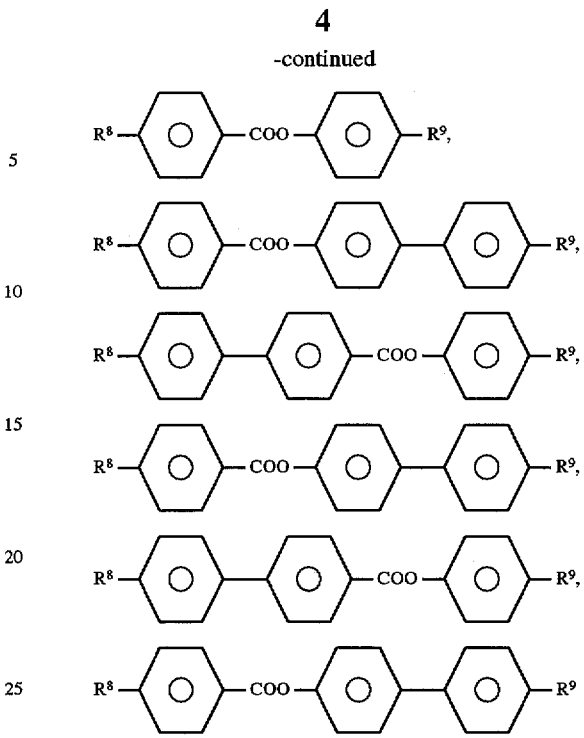

Further, as compounds to be added to such basic substances and inducing ferroelectricity, many compounds have been reported so far.

Examples of compounds having been used as such optically active raw materials are as follows:

2-methylbutanol, 2-octanol, lactic acid esters, 1-trifluoromethyl-1-heptanol, ethyl 4,4,4-trifluoro-3-hydroxybutanoate, amino acids such as isoleucine, epoxy octane, etc.

Further, a number of compounds for ferroelectric liquid crystal compositions using lactic acid as an optically active raw material have been tried. These compounds are mentioned below:

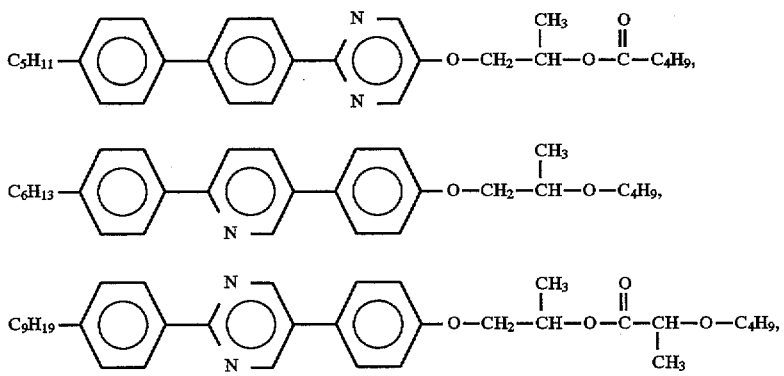

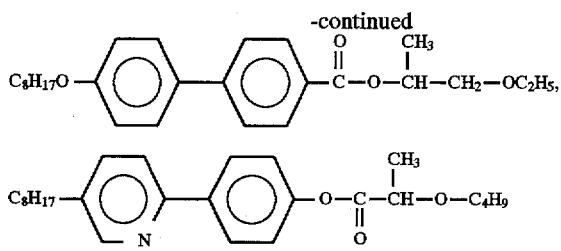

However, the ferroelectric liquid crystal display element has not yet been practically used, since the specific features required for the practical element could not have been satisfied by currently known compounds. The main cause consists in that optically active raw materials having been used so far have been limited.

The object of the present invention is to provide a novel optically active liquid crystal material by using a novel optically active raw material.

DISCLOSURE OF THE INVENTION

The present inventors have noted trifluorolactic acid esters as a novel optically active raw material in place of lactic acid esters. The compounds are those obtained by replacing the methyl group of lactic acid by trifluoromethyl group, and useful in the following aspects:

1. The compounds are bifunctional.

Both of the hydroxyl group and the ester group of the compounds are chemically convertible and the chemical bonding thereof to other parts is possible. Thus, the trifluorolactic acid esters have two parts where the bonding is possible; hence it is possible to introduce a structure having converted the trifluorolactic acid esters into not only the temrinal part of the chemical structure of liquid crystals, but also an optional intermediate position thereof. As a result, it is possible to prepare compounds abundant in the variety of chemical structure.

2. The compounds are provided with trifluoromethyl group.

The present inventors have often used lactic acid esters as a raw material for liquid crystal materials. As described above, trifluorolactic acid esters are trifluoro analogues of lactic acid. We have presumed that although the methyl group of lactic acid esters has a small electrical polarization, the trifluoromethyl group thereof has a large electric polarization. Thus, it is considered that the spontaneous polarization of liquid crystal materials derived from trifluorolactic acid is larger.

3. Three polar groups are bonded to one carbon atom.

The three polar groups refer to hydroxyl group, ester group and trifluoromethyl group. These three polar groups are bonded to one carbon atom; hence should it be possible to direct the direction of the electric polarization to one direction by adjusting the molecular structure, the dipole moment increases and as a result, it may be possible that the spontaneous polarization increases.

4. The claimed optically active trifluorolactic acid esters are novel.

The Chemical Abstract of Dialogue Co., Ltd. has been researched, and as a result, trifluorolactic acid esters have been found to have the following registry numbers:

|  | Absolute configuration | Registry number |
|---|---|---|
| Trifluorolactic acid |  +— | 648-07-1 |
| Trifluorolactic acid | R | 121250-04-2 |
| Methyl trifluorolactate | +— | 93496-85-6 |
| Methyl trifluorolactate | +— | 94725-99-2 |
| Ethyl trifluorolactate | +— | 94726-00-8 |
| Ethyl trifluorolactate | R | 121210-28-4 |

According to the above abstract, ethyl trifluorolactates have been regarded as already known, and the above ethyl trifluorolactate of registry No. 121210-28-4 has been regarded as described in Chemical Abstract III (4): 31747p, Japanese patent application laid-open No. Sho 64-3154.

However, trifluorolactic acid esters have not been described at all in the above Japanese patent application laid-open No. Sho 64-3154, and only ethyl trifluorohydroxybutyrate has been described therein. Further, the compounds described in the claims of the above laid-open application are those which cannot be derived from the trifluorolactic acid esters of the present application. Thus, it is seen that the description of the above Chemical Abstract is erroneous.

In view of the above fact, it is seen that the following optically active substance of trifluorolactic acid ester described in claim 6 of the present application is novel, and all of the compounds of the present application using the above novel raw material are also novel:

Further, the compounds described in claims 7 to 9 of the present application are also novel.

Namely, in the same manner as that in the case of the above trifluorolactic acid, the following compound described in claim 7 of the present application has been searched:

As a result, the following have been found:
132096-76-5
3,3,3-trifluoro-2-methoxy-Propanoic acid 1-ethyl-2-methylpentyl ester
(1S—(1R*(S*),2R*))—
Japanese patent application laid-open No. Hei 2-250840
127473-56-7
3,3,3-trifluoro-2-methoxy-Propanoic acid 2-methylbutyl ester (S—(R*,R*))—
Chem. Ber. (123) PAGES: 2023–30 1990
122751-27-3
3,3,3-trifluoro-2-methoxy-Propanoic acid 2-cyclopenten-1-yl ester
(R—(R*,R*))—
Japanese patent application laid-open No. Hei 1-6228
115793-08-3
3,3,3-trifluoro-2-methoxy-Propanoic acid 11-chloro-2,3,4,8a,9,13,14,17-octahydro-16-hydroxy-1,4-dimethoxy-12-methyl-14,17-dioxo-1H-xantheno(4',3',2':4,5)(1,3)benzodioxino(7,6-g)isoquinoline-3,15-diyl ester
(1S-(1.alpha.,3.alpha.(S*),4.beta.,8a.alpha.,15(S*)))—
J. Antibiot. (41) PAGES: 502–11 1988
115655-88-4
3,3,3-trifluoro-2-methoxy-Propanoic acid 11-chloro-2,3,4,8a,9,13,14,17-octahydro-16-hydroxy-1,4-dimethoxy-12-methyl-14, 17-dioxo-1H-xantheno(4',3',2':4,5)(1,3)-benzodioxino(7,6-g) isoquinoline-3,15-diyl ester
(1S-(1.alpha.,3.alpha.(R*),4.beta.,8a.alpha.,15(R*)))—
J. Antibiot. (41) PAGES: 502–11 1988

All of the above compounds are esters of 3,3,3-trifluoro-2-methoxy-propanoic acid.

The primary information sources of these compounds have been searched. As a result, it has been found that all of these compounds are ester derivatives of (R)-(+)-α-methoxy-α-(trifluoromethyl)phenylacetic acid (20445-31-2) or (S)-(−)-α-methoxy-α-(trifluoromethyl)phenylacetic acid (17257-71-5).

Thus, it is evident that the informations of the Chemical Abstract are erroneously described. Accordingly, it is seen that the compound in claim 7 of the present application is entirely novel.

Further, the following compound in claim 8 has been searched:

As a result, the following result has been obtained as a similar compound:
360-26-9
3-ethoxy-1,1,1-trifluoro-2-Propyl acetate In the case of the following compound in claim 9 of the present application:

the following compounds have been obtained as a result of search:
21511-97-7
3-(allyloxy)-1,1,1-trifluoro-2-Propanol
339-64-0
3-ethoxy-1,1,1-trifluoro-2-Propanol
339-54-8
2-ethoxy-3,3,3-trifluoro-1-Propanol.

All of these compounds, too, are not optically active. In order to induce the ferroelectricity, optically active compounds are required. Even if the above compounds are used as an intermediate of the present invention, it is impossible to induce the ferroelectricity.

Thus, it is seen that all compounds claimed in the present invention have novelty.

From the above four viewpoints, the present inventors have investigated optically active trifluorolactic acid esters.

Further, in advance of the present application, Japanese patent application laid-open No. Hei 2-131444 discloses a scope of patent claim including the compounds of the present application. The scope of patent claim will be described below.

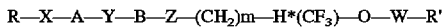

wherein R, X, A, Y, B, Z, m, W and R' are as defined in the above laid-open application.

Compounds Nos. 9–18 described in Table 1 of the above laid-open application as concrete examples of compounds expressed by the above formula accord with the optically active groups of the compounds of the present application.

However, it will be described below that the above laid-open application does not forfeit the "novelty" of the present application.

Firstly, the raw material used in the Examples of the laid-open application is only optically active 4-ethyloxy-5,5,5-trifluoropentylalcohol. Namely, the laid-open application discloses only Examples wherein the core therein has a m value of 3, but there are no Examples wherein the core has a m value of 1. Thus, any description suggesting the specific properties thereof is not made at all.

Secondly, the above laid-open application does not disclose at all the concrete preparation of the optically active raw material. Namely, the application does not disclose at all a concrete preparation example of the optically active alcohol as a raw material used for forming the compound of the present application (HO—(CH$_2$)$_m$—C*(CF$_3$)H—O—W—R' in the application). In the item of compound preparation, only an optically active alcohol containing trifluoromethyl group is abruptly described in the form of HO—(CH$_2$)$_m$—C*(CF$_3$)H—O—W—R'.

Thus, it is not disclosed in what manner the optically active alcohol wherein a m value is 1, as regarded as useful in the present invention, is available. Further, even as to the alcohol wherein a m value is 3, disclosed in Example, that is, optically active 4-ethyloxy-5,5,5-trifluoropentyl alcohol, its preparation is not described therein at all.

Thirdly, the data of physical properties of compounds obtained in Examples of the above laid-open application describe only phase transition points, but entirely do not describe other values of physical properties such as spontaneous polarization value, viscosity, etc. which are important values of physical properties for ferroelectric liquid crystal compounds. Further, the item of effectiveness in the above laid-open application is directed only to an abstract expression that there is a possibility that the spontaneous polarization value becomes larger, but it does not present at all an expression by way of concrete measurement values; in short, there is no description directed to advance of the invented compounds by way of comparison thereof with known compounds, etc.

In view of the above three aspects, it is concluded that the compounds described in the above laid-open application are those which generally express the cores of the compounds derived from an optically active raw material, 4-ethyloxy-5,5,5-trifluoropentylalcohol and have the considered cores arranged merely; hence there is entirely not observed any thought such as improvement in the spontaneous polarization value or viscosity in ferroelectric liquid crystals. Further, it is pointed out that Examples are very few as compared with the scope of patent claim.

Whereas, the present inventors have made extensive research in a structure having the dipole moment of trifluoromethyl group effectively contributed to the development of the spontaneous polarization of a compound. As a result, it has been found that a compound having a large spontaneous polarization value is such a compound as that having a m value of 1 in the above laid-open application, i.e. a compound having a structure wherein an asymmetric carbon atom having trifluoromethyl group bonded thereto is bonded to an oxygen atom directly bonded to an aromatic ring, through one methylene chain (see the formula (I)).

Further, in the present invention, the present inventors have prepared the core in the laid-open application wherein the m value is 1, for the first time by deriving therein an optically active trifluorolactic acid ester which has been a novel optically active raw material. Further, the present application also discloses a preparation process of the optically active trifluorolactic acid ester, in detail. Since the optically active trifluorolactic acid ester is not disclosed in the laid-open application, the present application can be regarded as entirely different from the laid-open application, in the aspects of the idea and the object.

Further, the present application, as described later in detail, clearly shows that the compound expressed by the formula (I) is provided with far superior specific features suitable to compounds for ferroelectric liquid crystals, to conventional compounds, in view of comparison of measurement values. In this respect, too, the present application can be regarded as different from Japanese patent application laid-open No. Hei 2-131444 regarding it as effective in an abstract expression.

In view of the foregoing, the compound of the present invention prepared by deriving it from an optically active trifluorolactic acid ester is entirely novel, and its novelty is not regarded as being forfeited by the above Hei 2-131444.

Namely, the present invention is characterized by an optically active compound of the below-mentioned formula (I) derived from an optically active trifluorolactic acid ester.

The present invention resides in a compound and a ferroelectric liquid crystal composition comprising the same, the above compound being expressed by the formula

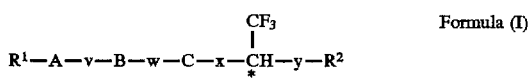

wherein $R^1$ represents either one of an alkyl group, or alkoxy group of 1 to 18 carbon atoms, or an alkanoyl group, alkanoyloxy group or alkoxycarbonyl group of 2 to 18 carbon atoms, $R^2$ represents an alkyl group which may be replaced by an alkoxy group (the total of the carbon atoms being 1 to 15), A, B and C each independently are selected from the group consisting of

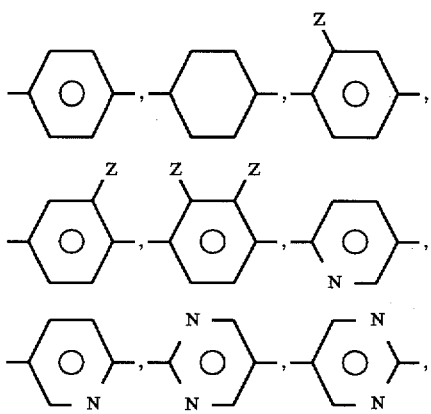

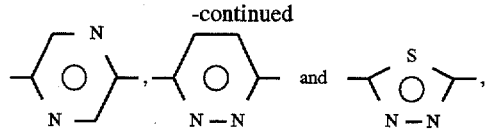

z represents a chlorine atom or a fluorine atom, v and w each independently are selected from the group consisting of —COO—, —OCO—, —CH$_2$O—, —OCH$_2$—, —CH$_2$CH$_2$—, —CH═CH—, —C≡C— and a single bond, and x and y each are selected from the following combinations consisting of —OCH$_2$— and —O—, —OCH$_2$— and —OCO—, —OCH$_2$— and —OCOO—, —OCO— and —O—, —OCO— and —OCO—, —OCO— and —OCOO—, —COO— and COO—, —COO— and —CO—, —COO— and —CH$_2$O—, —COO— and —CH$_2$OCO—, —COO— and —CH$_2$OCOO—, —COOCH$_2$— and —O—, —COOCH$_2$— and —OCO—, —COOCH2— and —OCOO—, —O— and —CH$_2$O—, —O— and —CH$_2$OCO—, —O— and —CH$_2$OCOO—.

The best embodiments for carrying out the present invention:

In the compounds expressed by the formula (I), $R^1$ is preferably an alkyl group or alkoxy group of 1 to 12 carbon atoms, more preferably those of 2 to 10 carbon atoms. Preferable, examples thereof are methyl, ethyl, propyl, butyl, pentyl, hexyl, heptyl, octyl, nonyl, decyl, methoxy, ethoxy, propoxy, butoxy, pentyloxy, hexyloxy, heptyloxy, octyloxy, nonyloxy, decyloxy, acetyl, propanoyl, butanoyl, pentanoyl, hexanoyl, heptanoyl, octanoyl, nonanoyl, acetoxy, propanoyloxy, butanoyloxy, pentanoyloxy, hexanoyloxy, heptanoyloxy, octanoyloxy, nonanoyloxy, methoxycarbonyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, etc.

$R^2$ is preferably an alkyl group of 1 to 12 carbon atoms, more preferably that of 2 to 10 carbon atoms. Preferable examples of $R^2$ are ethyl, propyl, butyl, pentyl, hexyl, heptyl, octyl, nonyl, decyl, etc. $R^1$ and $R^2$ each may contain methyl branch, ethyl branch, etc. In this case, those which can become optically active can also form optically active substances. As concerete examples thereof, the following alkyl group are mentioned:

1-methylpropyl, 1-methylbutyl, 1-methylpentyl, 1-methylhexyl, 1-methylheptyl, 1-methyloctyl, 1-methylnonyl, 1-methyldecyl, 1-methylundecyl, 1-methyldodecyl, 2-methylbutyl, 3-methylpentyl, 4-methylhexyl, 5-methylheptyl, 6-methyloctyl, 7-methylnonyl, 8-methyldecyl, etc.

The optically active raw material used in the present invention is compounds of the formula (II) and compounds of the formulas (III), (IV) and (V) as their derivatives.

Examples of $R^3$ in the compounds of the formula (II)

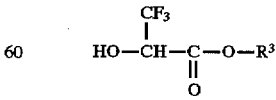

are an alkyl group or aralkyl group of 1 to 10 carbon atoms. Preferable examples of $R^3$ are methyl, ethyl, propyl, butyl, pentyl, hexyl, heptyl, octyl, nonyl, decyl, benzyl, 1-phenylethyl, etc.

R⁴ in the compound of the formula (III)

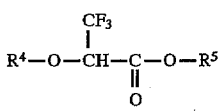

is an alkyl group, aralkyl group, alkanoyl group or alkoxycarbonyl group of 1 to 16 carbon atoms which may be substituted by an alkoxy group. These groups may form a ring form. Preferable examples of R⁴ are methyl, ethyl propyl, butyl, pentyl, hexyl, heptyl, octyl, nonyl, decyl, benzyl, 1-phenylethyl, acetyl, propanoyl, butanoyl, pentanoyl, hexanoyl, heptanoyl, octanoyl, nonanoyl, ethoxycarbonyl, propoxycarbonyl, butoxycarbonyl, pentyloxycarbonyl, hexyloxycarbonyl, heptyloxycarbonyl, octyloxycarbonyl, nonyloxycarbonyl, methoxymethyl, benzyloxymethyl, 1-ethoxyethyl, 2-ethoxyethyl, 1-methoxy-1-methylethyl, tert-butyl, 2-tetrahydropyranyl, 4-methoxy-5,6-tetrahydropyrane-4-yl, etc.

When R⁵ is equal to R³, it is ester, and preferable R³ at that time is the same as those already described. When R⁵ is a hydrogen atom, the above-mentioned compound is a carboxylic acid.

R⁶ in the compound of the formula (IV)

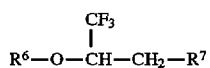

is an alkyl group or aralkyl group of 1 to 16 carbon atoms which may be substituted by an alkoxy group. They may form a ring form. Preferable examples of R⁶ are methyl, ethyl, propyl, butyl, pentyl, hexyl, heptyl, octyl, nonyl, decyl, benzyl, 1-phenylethyl, methoxymethyl, benzyloxymethyl, 1-ethoxyethyl, 2-ethoxyethyl, 1-methoxy-1-methylethyl, tert-butyl, 2-tetrahydropyranyl, 4-methoxy-5,6-tetrahydropyrane-4-yl, etc.

R⁷ is a hydroxyl group, a halogen atom, a methanesulfonyloxy group, a p-toluenesulfonyloxy group or a benzenesulfonyloxy group, and when R⁷ is a hydroxyl group, the above compound is an alcohol. When R⁷ is either one of a halogen atom, a methanesulfonyloxy group, a p-toluenesulfonyloxy group or a benzenesulfonyloxy group, they are usable as an reaction intermediate.

R⁵ in the compound of the formula (V)

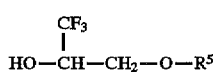

represents a hydrogen atom, an alkyl group or aralkyl group of 1 to 10 carbon atoms, and when it is a hydrogen atom, it forms diol; hence it is possible to use two hydroxyl groups for reaction. Further, when it is an alkyl group or aralkyl group of 1 to 10 carbon atoms, it forms an alcohol, and it forms a precursor just before liquid crystal compound.

In the compound of the formula (I) of the present invention, preferable examples of —A—v—B—w—C— are as follows:

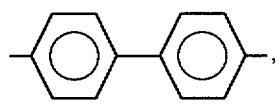

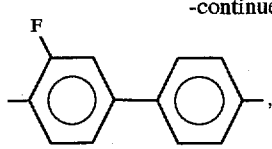

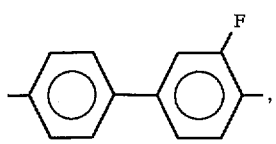

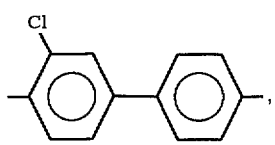

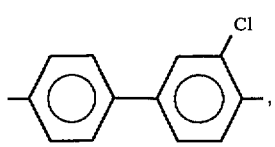

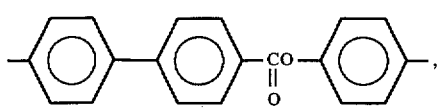

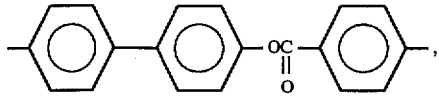

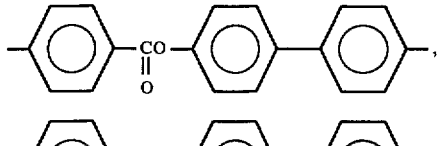

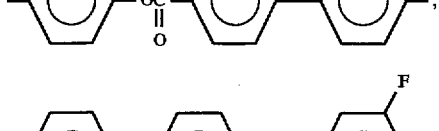

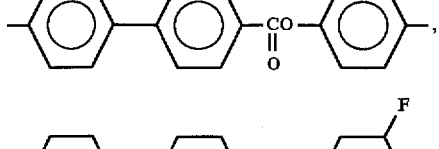

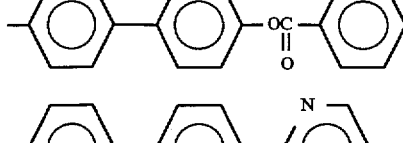

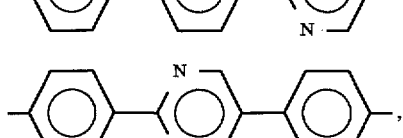

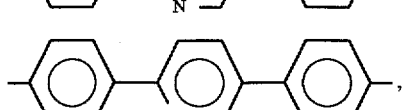

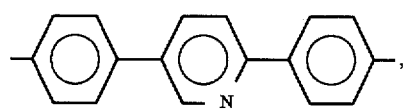
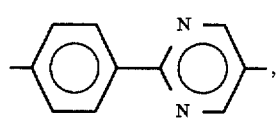
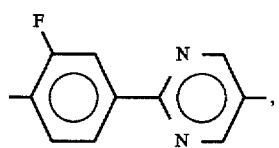
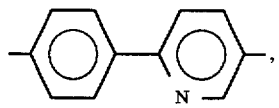
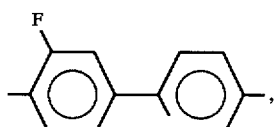
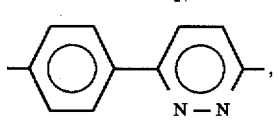
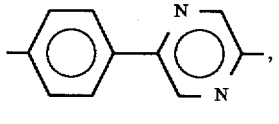
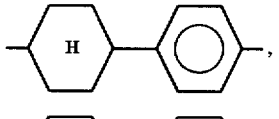
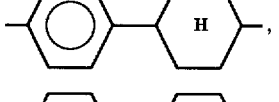
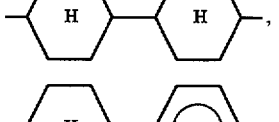
Preparation of Compound
The optically active trifluorolactic acid ester (compound described in claim 6) as a raw material of the present invention can be preferably prepared according to the following route:
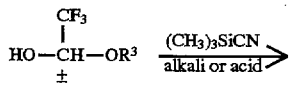
(1)
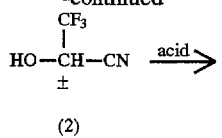
(2)
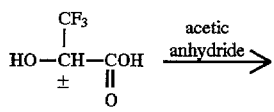
(3)
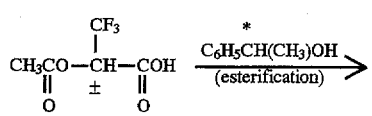
(4)
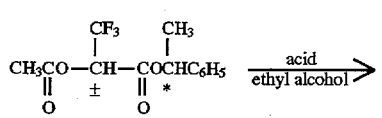
(5)
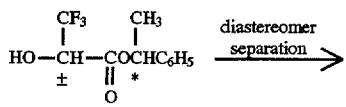
(6)
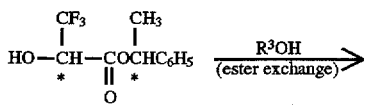
(7)
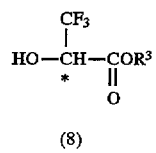
(8)
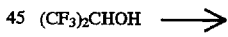
(9)
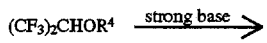
(10)
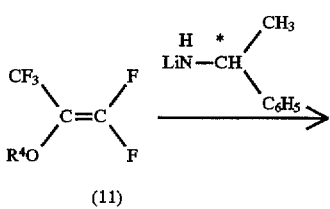
(11)
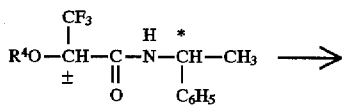
(12)

-continued
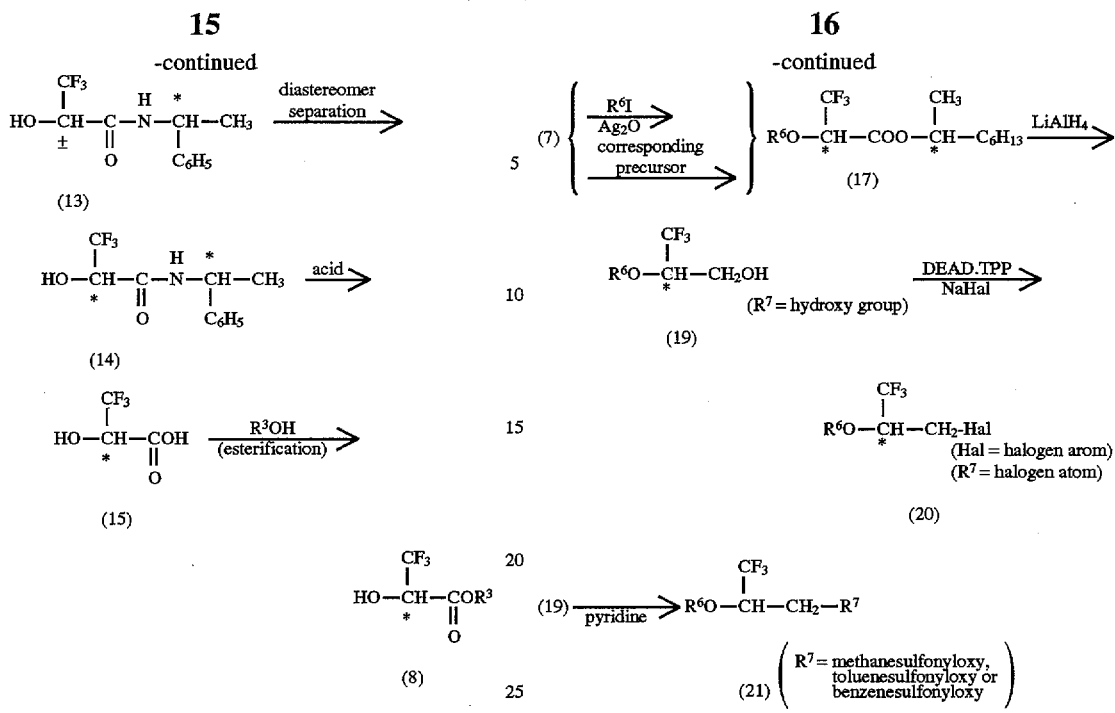
Preparation of Compound of the Formula (III)
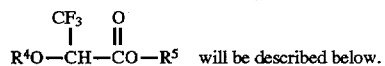
$R^4O\text{—CH—CO—}R^5$ will be described below.
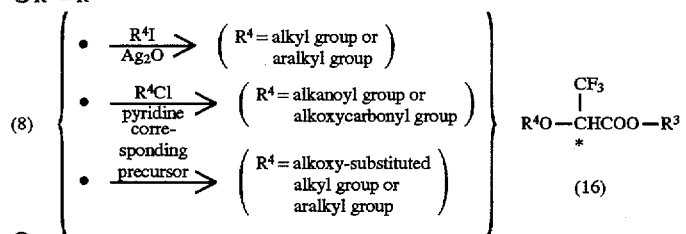
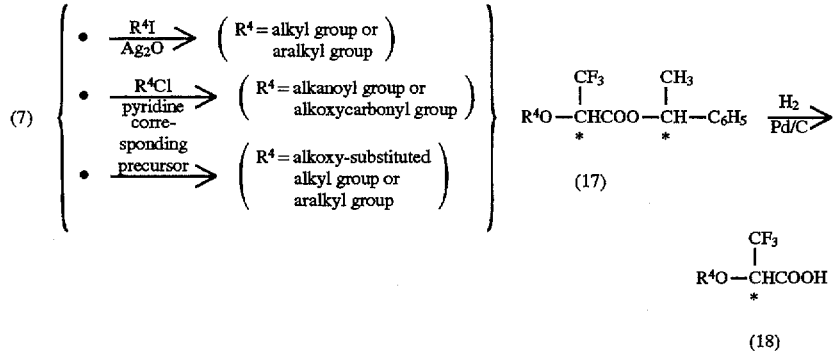
Preparation of the Compound of the Formula (IV)
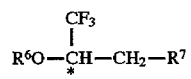
Preparation of the Compound of the Formula (V)
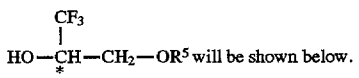 will be shown below.

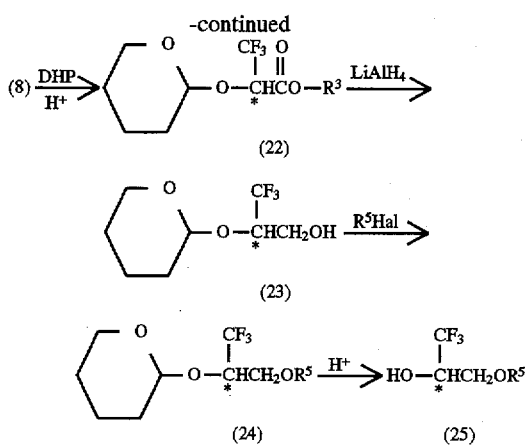

BRIEF DESCRIPTION OF THE DRAWINGS

FIG. 2 shows a view of 1H-NMR chart of the compound obtained in Example 14 of the present invention.

EXAMPLE

Figure 1:
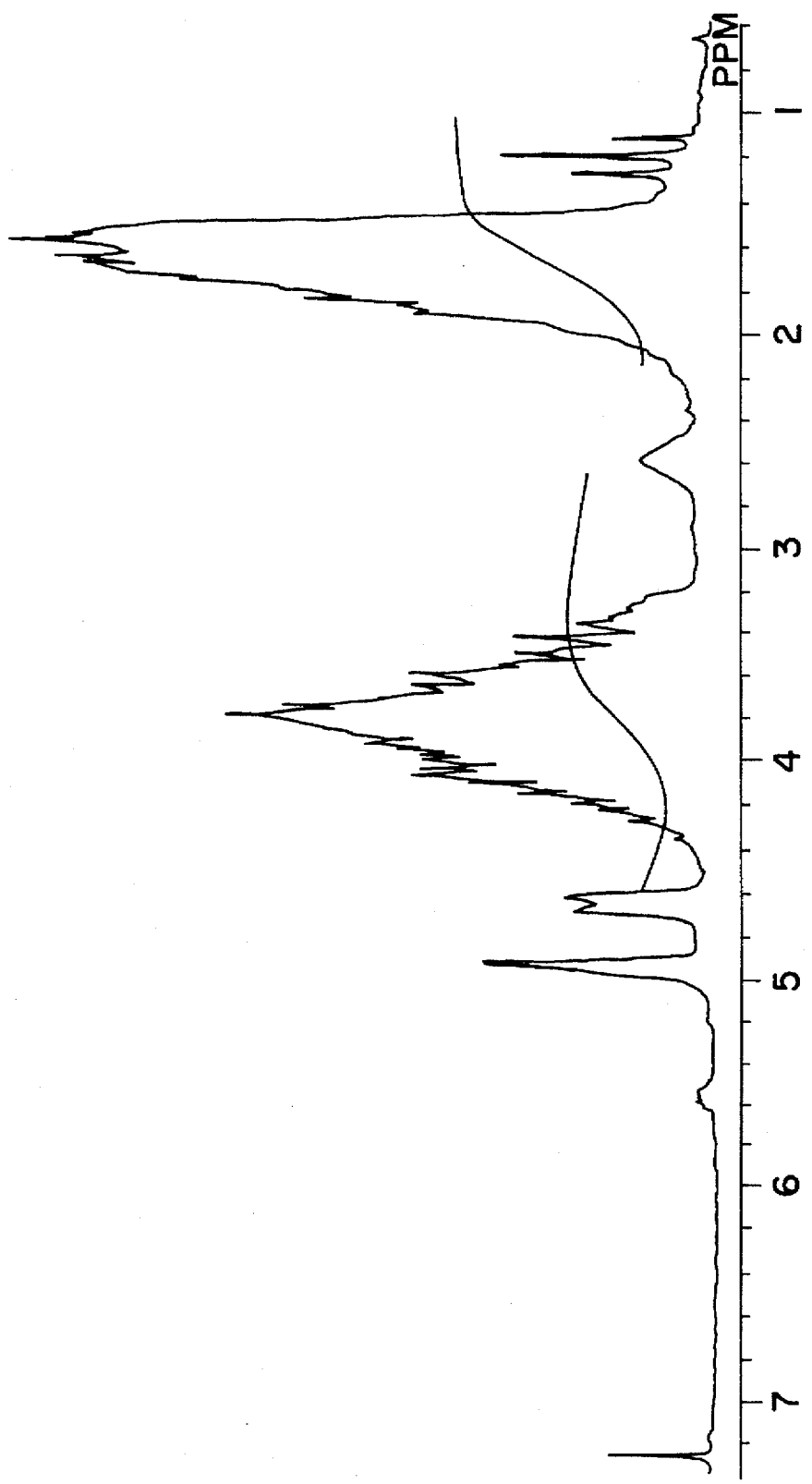
FIG. 1 shows a view of 1H-NMR chart of the compound obtained in Example 3 of the present invention.

The compound of the present invention will be described in more detail by way of Examples.

The measurement methods of the various physical properties of ferroelectric liquid crystals were carried out according to the following:

(1) The spontaneous polarization (Ps) was measured according to Sawyer-Tower method.

(2) The tilt angle (θ) was sought in terms of ½ of the movement angle between an extinction position at the time when an sufficiently high electric field of a critical voltage or higher was impressed to a homogeneously aligned cell and an extinction position at the time of polar inversion.

(3) The response time (τ) refers to the time of change in the intensity of the transmitted light obtained when a composition was enclosed in a cell of 10 μm thickness provided with transparent electrodes obtained by coating the surfaces with polyvinyl alcohol as an alignment-treating material, followed by rubbing the surfaces to subject to parallel aligning treatment, and a square wave of 10 V/μm and 100 Hz was impressed.

(4) The viscosity (η) was calculated from the half value width of peak of polarization inversion current curve and the spontaneous polarization value at the time of impression of a square wave (Jpn. J. Appl. Phys., 26, 1225 (1987)).

Further, Ps and η depend largely upon θ; hence in order that the measurement values do not depend upon θ, $P_o$ and $η_o$ having specified Ps by sin θ and η by sin 2θ, respectively, were established ($P_o$=Ps/sin θ and $η_o$=η/sin 2θ).

EXAMPLE 1

Preparation of Optically Active Ethyl Trifluorolactate (compound of $R^3$=ethyl in the compound (II) in claim 6)

First Step

Preparation of 1-cyano-2,2,2-trifluoroethanol (2)

A mixture of sodium hydride (49.9 g) with tetrahydrofuran (hereinafter abbreviated to THF) (1.5 g) was cooled with ice, followed by dropwise adding a THF (200 ml) solution of trifluoroacetaldehyde ethyl hemiacetal (1) (100 g), thereafter dropwise adding a THF (200 ml) solution of trimethylsilyl cyanide (75.4 g), raising the temperature up to room temperature, stirring the mixture for 2 hours, cooling the resulting reaction solution with ice, dropwise adding 2N hydrochloric acid (200 ml) to make the pH of the reaction solution 6, adding ether (500 ml), washing the organic layer with water, drying over anhydrous magnesium sulfate, filtering the anhydrous magnesium sulfate, concentrating, and distilling the residue under reduced pressure to obtain 1-cyano-2,2,2-trifluoroethanol (2) (75.8 g). b.p. 75° C. (44 mmHg).

Second Step

Preparation of trifluorolactic acid (racemic form (3))

A mixture of (2) obtained in the first step (50 g), conc. sulfuric acid (250 g) and water (100 ml) was heated under reflux for 3 hours, followed by allowing it to cool, adding ether (500 ml), washing the organic layer with water, drying it over anhydrous magnesium sulfate, filtering the anhydrous magnesium sulfate, concentrating and distilling the residue under reduced pressure to obtain trifluorolactic acid (racemic form (3)) (41.2 g). b.p. 62° C. (2 mm/Hg).

Third Step

Preparation of 2-acetoxy-3,3,3-trifluoropropionic acid (racemic form (4))

A mixture of the racemic form (3) (35 g) obtained at the second step, acetic anhydride (37.2 g) and N,N-dimethylformamide (hereinafter abbreviated to DMF) (0.9 g) was stirred at room temperature for 3 hours, followed by pouring the reaction solution into ice water, adding ether (500 ml), washing the organic layer with water, drying it over anhydrous magnesium sulfate, concentrating, and distilling the residue under reduced pressure, to obtain 2-acetoxy-3,3,3-trifluoropropionic acid (racemic form (4)) (39 g). b.p. 70° C. (1 mm/Hg).

Fourth Step

Preparation of (1'S,2RS)-2-acetoxy-3,3,3-trifluoropropionic acid 1'-phenylethyl ester (5)

A mixture of (S)-(-)-1-phenylethanol (28.1 g), dicyclohexylcarbodiimide (hereinafter abbreviated to DCC) (59.8 g), N,N-dimethylaminopyridine (hereinafter abbreviated to DMAP) (2.3 g) and methylene chloride (350 ml) was cooled with ice, followed by dropwise adding a methylene chloride (350 ml) solution of the racemic form (4) obtained in the above step, stirring the mixture at room temperature for 3 hours, removing the deposited solids by filtration, concentrating the mother, liquid, adding toluene (500 ml) to the residue, washing the organic layer with 6N hydrochloric acid, water, 2N NaOH aqueous solution and water in this order, drying over anhydrous sodium sulfate, concentrating, and distilling the residue under reduced pressure, to obtain (5) (37 g). b.p. 90° C. (1 mm Hg).

Fifth Step

Preparation of (1'S,2RS)-trifluorolactic acid 1'-phenylethyl ester (6)

A mixture of (5) obtained at the above step (24 g), ethyl alcohol (240 ml) and p-toluenesulfonic acid (3.1 g) was heated with stirring for 12 hours, followed by allowing it to cool, pouring it in an ice water (500 ml), adding ether (300 ml), separating the organic layer, concentrating it, and recrystallizing the residue with heptane, to obtain (6) (10 g). m.p. 76°–79° C.

Sixth Step

Separation of diastereomer (1'S,2RS)-trifluorolactic acid 1'-phenylethyl ester (6) (7 g) obtained at the fifth step was separated into diastereomer according to silica gel chromatography.

Diastereomer 1: yield (3.1 g), m.p. (79.5° C.), $[\alpha]_D^{28}$–108.1 (cl 04, CHCl$_3$).

Diastereomer 2: yield (3.3 g), m.p. (75.7° C.), $[\alpha]_D^{24}$–84.9 (cl. 01, CHCl$_3$).

Seventh Step

Preparation of (–)-trifluorolactic acid ethyl ester (compound of (8) wherein R$^3$=C$_2$H$_5$)

A mixture of diastereomer 1 obtained at the above step (2.3 g), ethyl alcohol (50 ml) and conc. sulfuric acid (0.6 g) was heated under reflux for 14 hours, followed by allowing it to cool, adding ether (200 ml), washing the organic layer with saturated NaCl solution, drying over magnesium sulfate, concentrating it and recrystallizing the residue with hexane, to obtain (–)-trifluorolactic acid ethyl ester (10 g) m.p 53.3° C. $[\alpha]_D^{28}$–31.0 (cl. 05, CHCl$_3$).

The proton NMR data of this compound were as follows:

| σ (ppm) | (TMS internal standard) |
|---|---|
| 4.4 | (q, 2H, J=7.0Hz) |
| 4.4 | (q, 1H, J=7.1Hz) |
| 3.4 | (d, 1H, J=7.7Hz) |
| 1.4 | (t, 3H, J=7.3Hz) |

The following compounds can be prepared in the same process as the above:
Optically active trifluorolactic acid methyl ester
Optically active trifluorolactic acid propyl ester
Optically active trifluorolactic acid isopropyl ester
Optically active trifluorolactic acid butyl ester
Optically active trifluorolactic acid isobutyl ester
Optically active trifluorolactic acid sec-butyl ester
Optically active trifluorolactic acid pentyl ester
Optically active trifluorolactic acid 2-methylbutyl ester
Optically active trifluorolactic acid hexyl ester
Optically active trifluorolactic acid heptyl ester
Optically active trifluorolactic acid octyl ester
Optically active trifluorolactic acid nonyl ester
Optically active trifluorolactic acid decyl ester
Optically active trifluorolactic acid benzyl ester
Optically active trifluorolactic acid phenetyl ester

EXAMPLE 2

Preparation of Optically Active Ethyl 2-(2-tetrahydropyranyloxy)-3,3,3-trifluoropropionate (compound (III) of claim 7 wherein R$^4$=2-tetrahydropyranyl group and R$^5$=ethyl)

A mixture of (–)-trifluorolactic acid ethyl (2.8 g) obtained at the seventh step of Example 1, 3-dihydro-4H-pyrane (hereinafter abbreviated to DHP) and methylene chloride (20 ml) was stirred under ice cooling, followed by dropwise adding a mixed solution of pyridium p-toluenesulfonate (hereinafter abbreviated to PPTs) (0.08 g) with methylene chloride (10 ml), stirring the mixture overnight, adding sodium hydrogen carbonate (0.04 g), stirring the mixture for one hour, removing the solvent, purifying the residue by a silica gel column and drying it by a vacuum pump. Yield: 4.0 g.

EXAMPLE 3

Preparation of Optically Active 2-(2-tetrahydropyranyloxy)-3,3,3-trifluoro-1-propanol (a compound (IV) of claim 8 wherein R$^6$=2-tetrahydropyranyl group, R$^7$=hydroxyl group)

A mixture of lithium aluminum hydride (0.44 g) with THF (10 ml) was stirred under ice cooling, followed by gradually dropwise adding a mixed solution of the ester obtained in Example 2 (4.0 g) with THF (15 ml), raising the temperature up to room temperature, stirring the mixture for one hour, again cooling with ice, dropwise adding ethyl acetate (0.8 g) and 2N NaOH aqueous solution in this order, filtering off the deposited material, extracting with ether (100 ml), washing with saturated NaCl aqueous solution, drying over anhydrous magnesium sulfate and removing the solvent. Yield: 3.2 g.

The 1H-NMR chart of this compound is shown in FIG. 1.

By replacing DHP in Example 2 by ethyl vinyl ether, the following compounds can be prepared:
ethyl 2-(1-ethoxyethyl)-3,3,3-trifluoropropionate
2-(1-ethoxyethyl)-3,3,3-trifluoro-1-propanol By replacing DHP in Example 2 by 2-methoxypropene, the following compounds can be prepared:
ethyl 2-(1-methoxy-1-methylethyl)-3,3,3-trifluoropropionate
2-(1-methoxy-1-methylethyl)-3,3,3-trifluoro-1-propanol By replacing DHP in Example 2 by 4-methoxy-5,6-dihydro-2H-pyrane, the following compounds can be prepared:
ethyl 2-(4-methoxy-5,6-tetrahydropyran-4-yl)-3,3,3-trifluoropropionate
2-(4-methoxy-5,6-tetrahydropyran-4-yl)-3,3,3-trifluoro-1-propanol.

EXAMPLE 4

Preparation of Optically Active 1-trifluoromethyl-2-ethoxyethanol (compound (V) of claim 9 wherein R$^5$=ethyl)

A mixture of sodium hydride (340 mg) with THF (30 ml) was stirred under ice cooling, followed by dropwise adding a mixture of the alcohol obtained in Example (1 g) with THF (10 ml), further adding a mixture of ethyl iodide with THF (10 ml), stirring the resulting mixture under ice cooling for 3 hours, stirring at room temperature for 3 hours, extracting with diethyl ether (100 ml), washing with 2N NaOH aqueous solution, neutralizing, washing with water, removing the solvent, drying by a vacuum pump, heating a mixture of the resulting compound, with p-toluenesulfonic acid (50 mg) and ethanol (30 ml) with stirring for 2 hours, extracting with ether, neutralizing, washing with water, removing the solvent and drying by a vacuum pump to obtain an objective substance (550 mg).

In the same manner as the above, the following compounds of claim 9 can be prepared:
optically active 1-trifluoromethyl-2-methoxyethanol
optically active 1-trifluoromethyl-2-propoxyethanol
optically active 1-trifluoromethyl-2-butoxyethanol
optically active 1-trifluoromethyl-2-pentyloxyethanol
optically active 1-trifluoromethyl-2-hexyloxyethanol
optically active 1-trifluoromethyl-2-heptyloxyethanol optically active 1-trifluoromethyl-2-octyloxyethanol
optically active 1-trifluoromethyl-2-nonyloxyethanol
optically active 1-trifluoromethyl-2-decyloxyethanol
optically active 1-trifluoromethyl-2-benzylethanol
optically active 1-trifluoromethyl-2-phenethylethanol

EXAMPLE 5

Preparation of 1'-phenylethyl 2-butoxy-3,3,3-trifluoropropionate (compound III of claim 7 wherein $R^4$=butyl and $R^5$=phenethyl A mixture of trifluorolactic acid 1'-phenylethyl ester (4.0 g) obtained at the fifth step of Example 1, butyl iodide (3.5 g), silver oxide (4.1 g) and toluene (10 ml) was stirred overnight, followed by filtering off the solids, washing the mother liquor with an alkali, neutralizing, washing and distilling udner reduced pressure to obtain 1'-phenylethyl 2-butoxy-3,3,3-trifluoropropionate. Its absolute configuration is (2S,1'S).

In the same manner as the above, the following compounds of claim 7 can be prepared:
1'-phenylethyl 2-methoxy-3,3,3-trifluoropropionate
1'-phenylethyl 2-ethoxy-3,3,3-trifluoropropionate
1'-phenylethyl 2-propoxy-3,3,3-trifluoropropionate
1'-phenylethyl 2-pentyloxy-3,3,3-trifluoropropionate (2R, 1'R), b.p. 147 (8.5 mmHg), [α] −90.9
1'-phenylethyl 2-hexyloxy-3,3,3-trifluoropropionate
1'-phenylethyl 2-heptyloxy-3,3,3-trifluoropropionate
1'-phenylethyl 2-octyloxy-3,3,3-trifluoropropionate
1'-phenylethyl 2-nonyloxy-3,3,3-trifluoropropionate
1'-phenylethyl 2-decyloxy-3,3,3-trifluoropropionate

EXAMPLE 6

Preparation of (+)-2-butoxy-3,3,3-trifluoropropionic acid (compound (III) of claim 7 wherein $R^4$=butyl and $R^5$=hydrogen atom)

Using the ester (3 g) obtained in Example 5 and Pd-on-C catalyst, hydrogenation reaction was carried out, followed by distillation under reduced pressure to obtain 2-butoxy-3,3,3-trifluoropropionic acid (1.5 g) (99 (8 mmHg)). [α] +17.67 (cl. 06, CHCl$_3$).

In the same manner as the above, the following compounds of claim 7 can be prepared:
2-methoxy-3,3,3-trifluoropropionic acid
2-ethoxy-3,3,3-trifluoropropionic acid
2-propoxy-3,3,3-trifluoropropionic acid
(−)-2-pentyloxy-3,3,3-trifluoropropionic acid [α] −15.0 (cl. 1, CHCl$_3$).
2-hexyloxy-3,3,3-trifluoropropionic acid
2-heptyloxy-3,3,3-trifluoropropionic acid
2-octyloxy-3,3,3-trifluoropropionic acid
2-nonyloxy-3,3,3-trifluoropropionic acid
2-decyloxy-3,3,3-trifluoropropionic acid

EXAMPLE 7

Preparation of (+)-ethyl 2-butoxy-3,3,3-trifluoropropionate (compound (III) of claim 7 wherein $R^4$=butyl and $R^5$=ethyl)

A mixed solution of (+)-2-butoxy-3,3,3-trifluoropropionic acid (1.2 g) obtained in Example 6, ethanol (40 ml) and p-toluenesulfonic acid monohydrate (0.1 g) was heated with stirring for 12 hours, followed by distilling off the solvent under normal pressure, extracting the residue with ether, neutralizing, washing with water and concentrating to obtain (+)-ethyl 2-butoxy-3,3,3-trifluoropropionate (0.9 g). [α] +24.1 (cl. 06, CHCl$_3$).

In the same manner as the above, the following compounds of claim 7 can be prepared:
methyl 2-butoxy-3,3,3-trifluoropropionate
propyl 2-butoxy-3,3,3-trifluoropropionate
butyl 2-butoxy-3,3,3-trifluoropropionate
methyl 2-methoxy-3,3,3-trifluoropropionate
ethyl 2-methoxy-3,3,3-trifluoropropionate
propyl 2-methoxy-3,3,3-trifluoropropionate
butyl 2-methoxy-3,3,3-trifluoropropionate
methyl 2-ethoxy-3,3,3-trifluoropropionate
ethyl 2-ethoxy-3,3,3-trifluoropropionate
propyl 2-ethoxy-3,3,3-trifluoropropionate
butyl 2-ethoxy-3,3,3-trifluoropropionate
methyl 2-propoxy-3,3,3-trifluoropropionate
ethyl 2-propoxy-3,3,3-trifluoropropionate
propyl 2-propoxy-3,3,3-trifluoropropionate
butyl 2-propoxy-3,3,3-trifluoropropionate
methyl 2-pentyloxy-3,3,3-trifluoropropionate
ethyl 2-pentyloxy-3,3,3-trifluoropropionate
propyl 2-pentyloxy-3,3,3-trifluoropropionate
butyl 2-pentyloxy-3,3,3-trifluoropropionate
methyl 2-hexyloxy-3,3,3-trifluoropropionate
ethyl 2-hexyloxy-3,3,3-trifluoropropionate
propyl 2-hexyloxy-3,3,3-trifluoropropionate
butyl 2-hexyloxy-3,3,3-trifluoropropionate
methyl 2-heptyloxy-3,3,3-trifluoropropionate
ethyl 2-heptyloxy-3,3,3-trifluoropropionate
propyl 2-heptyloxy-3,3,3-trifluoropropionate
butyl 2-heptyloxy-3,3,3-trifluoropropionate
methyl 2-octyloxy-3,3,3-trifluoropropionate
ethyl 2-octyloxy-3,3,3-trifluoropropionate
propyl 2-octyloxy-3,3,3-trifluoropropionate
butyl 2-octyloxy-3,3,3-trifluoropropionate

EXAMPLE 8

Preparation of (−)-2-butoxy-3,3,3-trifluoro-1-propanol (compound (IV) of claim 8 wherein $R^6$=butyl and $R^7$=hydroxyl group)

A mixture of lithium aluminum hydride (0.1 g) with THF (10 ml) was stirred under ice cooling, followed by gradually dropwise adding a mixed solution of (+)-ethyl 2-butoxy-3,3,3-trifluoropropionate (0.8 g) obtained in Example 7 with THF (5 ml), followed by raising the temperature up to room temperature, stirring for one hour, again cooling with ice, dropwise adding 2N NaOH aqueous solution, filtering off deposited substance, extracting with ether (50 ml), washing with saturated NaCl aqueous solution, drying over anhydrous magnesium sulfate and removing the solvent. Yield: 0.5 g. [α] −11.7 (cl. 0, CHCl$_3$)

In the same manner as the above, the following compounds of claim 8 can be prepared:
2-methoxy-3,3,3-trifluoro-1-propanol
2-ethoxy-3,3,3-trifluoro-1-propanol
2-pentoxy-3,3,3-trifluoro-1-propanol
2-pentyloxy-3,3,3-trifluoro-1-propanol
2-hexyloxy-3,3,3-trifluoro-1-propanol
2-heptyloxy-3,3,3-trifluoro-1-propanol
2-octyloxy-3,3,3-trifluoro-1-propanol
2-nonyloxy-3,3,3-trifluoro-1-propanol
2-decyloxy-3,3,3-trifluoro-1-propanol

EXAMPLE 9

Preparation of Optically Active 1-trifluoromethyl-2-ethoxyethyl 4'-octyloxy-4-biphenylcarboxylate (compound of the formula (I) wherein $R^1$=octyloxy, A=B=phenylene, C=single bond, v=w=single bond, x=—COO—, y=—CH$_2$O— and $R^2$=ethyl)

A mixture of trifluoromethyl-2-ethoxyethanol (200 mg) obtained in Example 4, DCC (300 mg), DMAP (30 mg) and methylene chloride (15 ml) was stirred under ice cooling, followed by dropwise adding a solution of 4'-octyloxybiphenyl-4-carboxylic acid (400 mg) and methylene chloride (20 ml), stirring for 2 hours, filtering off deposited solids, concentrating mother liquid, purifying the residue according to silica gel chromatography and recrystallizing from ethanol, to obtain the captioned optically active 1-trifluoromethyl-2-ethoxyethyl 4'-octyloxy-4-biphenylcarboxylate. Yield: 240 mg. m.p. 25.9° C.

In the same manner as the above, the following compounds are obtained.

1-trifluoromethyl-2-methoxyethyl 4'-hexyloxy-4-biphenylcarboxylate
1-trifluoromethyl-2-methoxyethyl 4'-octyloxy-4-biphenylcarboxylate
1-trifluoromethyl-2-methoxyethyl 4'-nonyloxy-4-biphenylcarboxylate
1-trifluoromethyl-2-methoxyethyl 4'-heptyl-4-biphenylcarboxylate
1-trifluoromethyl-2-methoxyethyl 4'-octyl-4-biphenylcarboxylate
1-trifluoromethyl-2-ethoxyethyl 4'-hexyl-4-biphenylcarboxylate
1-trifluoromethyl-2-ethoxyethyl 4'-octyloxy-4-biphenylcarboxylate
1-trifluoromethyl-2-ethoxyethyl 4'-decyloxy-4-biphenylcarboxylate
1-trifluoromethyl-2-ethoxyethyl 4'-heptyl-4-biphenylcarboxylate
1-trifluoromethyl-2-ethoxyethyl 4'-nonyl-4-biphenylcarboxylate
1-trifluoromethyl-2-propoxyethyl 4'-hexyloxy-4-biphenylcarboxylate
1-trifluoromethyl-2-propoxyethyl 4'-octyloxy-4'-biphenylcarboxylate
1-trifluoromethyl-2-propoxyethyl 4'-nonytoxy-4-biphenylcarboxylate
1-trifluoromethyl-2-propoxyethyl 4'-heptyl-4'-biphenylcarboxylate
1-trifluoromethyl-2-propoxyethyl 4'-decyl-4'-biphenylcarboxylate
1-trifluoromethyl-2-butoxyethyl 4'-hexyloxy-4-biphenylcarboxylate
1-trifluoromethyl-2-butoxyethyl 4'-nonyloxy-4-biphenylcarboxylate
1-trifluoromethyl-2-butoxyethyl 4'-octyl-4-biphenylcarboxylate
1-trifluoromethyl-2-methoxyethyl 4-(5-hexyloxypyrimidine-2-yl)benzoate
1-trifluoromethyl-2-methoxyethyl 4-(5-octyloxypyrimidine-2-yl)benzoate
1-trifluoromethyl-2-methoxyethyl 4-(5-decyloxypyrimidine-2-yl)benzoate
1-trifluoromethyl-2-methoxyethyl 4-(5-heptylpyrimidine-2-yl)benzoate
1-trifluoromethyl-2-methoxyethyl 4-(5-octylpyrimidine-2-yl)benzoate
1-trifluoromethyl-2-ethoxyethyl 4-(5-hexyloxypyrimidine-2-yl)benzoate
1-trifluoromethyl-2-ethoxyethyl 4-(5-heptyloxypyrimidine-2-yl)benzoate
1-trifluoromethyl-2-ethoxyethyl 4-(5-nonyloxypyrimidine-2-yl)benzoate
1-trifluoromethyl-2-ethoxyethyl 4-(5-hexylpyrimidine-2-yl)benzoate
1-trifluoromethyl-2-ethoxyethyl 4-(5-octylpyrimidine-2-yl)benzoate
1-trifluoromethyl-2-ethoxyethyl 4-(5-nonylpyrimidine-2-yl)benzoate
1-trifluoromethyl-2-propoxyethyl 4-(5-hexyloxypyrimidine-2-yl)benzoate
1-trifluoromethyl-2-propoxyethyl 4-(5-heptyloxypyrimidine-2-yl)benzoate
1-trifluoromethyl-2-propoxyethyl 4-(5-nonyloxypyrimidine-2-yl)benzoate
1-trifluoromethyl-2-propoxyethyl 4-(5-hexylpyrimidine-2-yl)benzoate
1-trifluoromethyl-2-propoxyethyl 4-(5-octylpyrimidine-2-yl)benzoate
1-trifluoromethyl-2-butoxyethyl 4-(5-hexyloxypyrimidine-2-yl)benzoate
1-trifluoromethyl-2-butoxyethyl 4-(5-octyloxypyrimidine-2-yl)benzoate
1-trifluoromethyl-2-butoxyethyl 4-(5-decyloxypyrimidine-2-yl)benzoate
1-trifluoromethyl-2-butoxyethyl 4-(5-hexylpyrimidine-2-yl)benzoate
1-trifluoromethyl-2-butoxyethyl 4-(5-octylpyrimidine-2-yl)benzoate
1-trifluoromethyl-2-butoxyethyl 4-(5-nonylpyrimidine-2-yl)benzoate
1-trifluoromethyl-2-methoxyethyl 4-(5-hexyloxypyridine-2-yl)benzoate
1-trifluoromethyl-2-methoxyethyl 4-(5-heptyloxypyridine-2-yl)benzoate
1-trifluoromethyl-2-methoxyethyl 4-(5-nonyloxypyridine-2-yl)benzoate
1-trifluoromethyl-2-methoxyethyl 4-(5-hexylpyridine-2-yl)benzoate
1-trifluoromethyl-2-methoxyethyl 4-(5-octylpyridine-2-yl)benzoate
1-trifluoromethyl-2-methoxyethyl 4-(5-nonylpyrldine-2-yl)benzoate
1-trifluoromethyl-2-ethoxyethyl 4-(5-heptyloxypyridine-2-yl)benzoate
1-trifluoromethyl-2-ethoxyethyl 4-(5-octyloxypyridine-2-yl)benzoate
1-trifluoromethyl-2-ethoxyethyl 4-(5-decyloxypyridine-2-yl)benzoate
1-trifluoromethyl-2-ethoxyethyl 4-(5-hexylpyridine-2-yl)benzoate
1-trifluoromethyl-2-ethoxyethyl 4-(5-octylpyridine-2-yl)benzoate
1-trifluoromethyl-2-propoxyethyl 4-(5-hexylpyridine-2-yl)benzoate
1-trifluoromethyl-2-propoxyethyl 4-(5-octylpyridine-2-yl)benzoate
1-trifluoromethyl-2-propoxyethyl 4-(5-nonyl-pyridine-2-yl)benzoate
1-trifluoromethyl-2-butoxyethyl 4-(5-octyloxypyridine-2-yl)benzoate
1-trifluoromethyl-2-butoxyethyl 4-(5-decyloxypyridine-2-yl)benzoate
1-trifluoromethyl-2-butoxyethyl 4-(5-nonyl-pyridine-2-yl)benzoate
1-trifluoromethyl-2-methoxyethyl 2-(4-hexyloxy-phenyl)pyrimidine-5-carboxylate
1-trifluoromethyl-2-methoxyethyl 2-(4-octyloxyphenyl)pyrimidine-5-carboxylate
1-trifluoromethyl-2-methoxyethyl 2-(4-heptylphenyl)pyrimidine-5-carboxylate
1-trifluoromethyl-2-methoxyethyl 2-(4-nonyl-phenyl)pyrimidine-5-carboxylate
1-trifluoromethyl-2-ethoxyethyl 2-(4-heptyloxyphenyl)pyrimidine-5-carboxylate 1-trifluoromethyl-2-ethoxyethyl 2-(4-octyloxyphenyl) pyrimidine-5-carboxylate
1-trifluoromethyl-2-ethoxyethyl 2-(4-hexyl-phenyl) pyrimidine-5-carboxylate
1-trifluoromethyl-2-ethoxyethyl 2-(4-nonyl-phenyl) pyrimidine-5-carboxylate
1-trifluoromethyl-2-propoxyethyl 2-(4-hexyloxyphenyl) pyrimidine-5-carboxylate
1-trifluoromethyl-2-propoxyethyl 2-(4-heptyloxyphenyl) pyrimidine-5-carboxylate
1-trifluoromethyl-2-propoxyethyl 2-(4-nonyloxyphenyl) pyrimidine-5-carboxylate
1-trifluoromethyl-2-propoxyethyl 2-(4-hexyl-phenyl) pyrimidine-5-carboxylate
1-trifluoromethyl-2-propoxyethyl 2-(4-octyl-phenyl) pyrimidine-5-carboxylate
1-trifluoromethyl-2-propoxyethyl 2-(4-decyl-phenyl) pyrimidine-5-carboxylate
1-trifluoromethyl-2-butoxyethyl 2-(4-heptyloxyphenyl) pyrimidine-5-carboxylate
1-trifluoromethyl-2-butoxyethyl 2-(4-octyloxyphenyl) pyrimidine-5-carboxylate
1-trifluoromethyl-2-butoxyethyl 2-(4-decyloxyphenyl) pyrimidine-5-carboxylate
1-trifluoromethyl-2-butoxyethyl 2-(4-octyl-phenyl) pyrimidine-5-carboxylate
1-trifluoromethyl-2-butoxyethyl 2-(4-nonyl-phenyl) pyrimidine-5-carboxylate
1-trifluoromethyl-2-methoxyethyl 4-(4-(5-hexyloxypyrimidine-2-yl)benzoyloxy)benzoate
1-trifluoromethyl-2-methoxyethyl 4-(4-(5-nonyloxypyrimidine-2-yl)benzoyloxy)benzoate
1-trifluoromethyl-2-methoxyethyl 4-(4-(5-hexylpyrimidine-2-yl)benzoyloxy)benzoate
1-trifluoromethyl-2-methoxyethyl 4-(4-(5-nonylpyrimidine-2-yl)benzoyloxy)benzoate
1-trifluoromethyl-2-ethoxyethyl 4-(4-(5-heptyloxypyrimidine-2-yl)benzoyloxy)benzoate
1-trifluoromethyl-2-ethoxyethyl 4-(4-(5-octyloxypyrimidine-2-yl)benzoyloxy)benzoate
1-trifluoromethyl-2-ethoxyethyl 4-(4-(5-hexylpyrimidine-2-yl)benzoyloxy)benzoate
1-trifluoromethyl-2-ethoxyethyl 4-(4-(5-heptylpyrimidine-2-yl)benzoyloxy)benzoate
1-trifluoromethyl-2-ethoxyethyl 4-(4-(5-nonylpyrimidine-2-yl)benzoyloxy)benzoate
1-trifluoromethyl-2-propoxyethyl 4-(4-(5-hexyloxypyrimidine-2-yl)benzoyloxy)benzoate
1-trifluoromethyl-2-propoxyethyl 4-(4-(5-octyloxypyrimidine-2-yl)benzoyloxy)benzoate
1-trifluoromethyl-2-propoxyethyl 4-(4-(5-nonyloxypyrimidine-2-yl)benzoyloxy)benzoate
1-trifluoromethyl-2-propoxyethyl 4-(4-(5-heptylpyrimidine-2-yl)benzoyloxy)benzoate
1-trifluoromethyl-2-propoxyethyl 4-(4-(5-decylpyrimidine-2-yl)benzoyloxy)benzoate
1-trifluoromethyl-2-butoxyethyl 4-(4-(5-octyloxypyrimidine-2-yl)benzoyloxy)benzoate

EXAMPLE 10

Preparation of Optically Active 3,3,3-trifluoro-2-pentanoyloxypropyl 4-(4-octyloxyphenyl)benzoate (compound of the formula (I) wherein $R^1$=octyloxy, A=B=1,4-phenylene, C=single bond, v=w=single bond, x=—COO—, y=—OCO— and $R^2$=butyl)

First Step

Preparation of 1-trifluoromethyl-2-(4-(4-octyloxyphenyl)benzoyloxyethanol

A mixture of the alcohol (200 mg) obtained in Example 3, DCC (230 mg), DMAP (20 g) and methylene chloride (15 ml) was stirred under ice cooling, followed by dropwise adding a solution of 4-(4-octyloxyphenyl)benzoic acid (330 mg) and methylene chloride (20 ml), stirring the mixture for 2 hours, filtering off deposited solids, concentrating the mother liquid, purifying the residue according to silica gel column chromatography and drying the residue by a vacuum pump. Yield: 360 mg. Thereafter, a mixture of this compound, p-toluenesulfonic acid (20 mg) and toluene (10 ml) was heated with stirring for 2 hours, followed by cooling, extracting with diethyl ether, neutralizing, washing with water, removing the solvent and recrystallizing the residue from a mixed solvent of heptane 3: toluene 2. Yield: 210 mg.

Second Step

Preparation of the Captioned Compound

A mixture of the compound obtained at the above step (100 mg), DCC (60 mg), DMAP (2 mg) and methylene chloride (10 ml) was stirred under ice cooling, followed by dropwise adding a mixed solution of pentanoic acid (30 mg) and methylene chloride (10 ml), stirring the mixture for 2 hours, filtering off deposited solids, concentrating the mother liquid, purifying the residue according to silica gel column chromatography and recrystallizing the residue from ethanol. Yield: 100 mg. m.p. 47° C.

In the same manner as the above, the following compounds can be prepared:

3,3,3-trifluoro-2-butanoyloxypropyl 4-(4-octylphenyl) benzoate
3,3,3-trifluoro-2-butanoyloxypropyl 4-(4-octylphenyl) benzoate
3,3,3-trifluoro-2-butanoyloxypropyl 4-(4-octylphenyl) benzoate
3,3,3-trifluoro-2-butanoyloxypropyl 4-(4-octylphenyl) benzoate
3,3,3-trifluoro-2-butanoyloxypropyl 4-(5-hexylpyrimidine-2-yl)benzoate
3,3,3-trifluoro-2-butanoyloxypropyl 4-(5-hexylpyrimidine-2-yl)benzoate
3,3,3-trifluoro-2-butanoyloxypropyl 4-(5-hexylpyrimidine-2-yl)benzoate
3,3,3-trifluoro-2-butanoyloxypropyl 4-(5-hexylpyrimidine-2-yl)benzoate

EXAMPLE 11

Preparation of Optically Active Ethyl 2-(4'-octyloxybiphenylyl-4-carboxyl)-3,3,3-trifluoropropionate (Compound of the formula (I) wherein $R^1$=octyloxy, A=B=phenylene, C=single bond, v=w=single bond, x=—COO—, y=—COO— and $R^2$=ethyl)

A mixture of (−)-ethyl trifluorolactate obtained in Example 1 (50 mg), DCC (72 mg), DMAP (3.7 mg) and methylene chloride (15 ml) was stirred under ice cooling, followed by dropwise adding a solution of 4'-octyloxybiphenyl-4-carboxylic acid (400 mg) with methylene chloride (20 ml), stirring the mixture for 2 hours, filtering off deposited solids, concentrating the mother liquid, purifying the residue according to silica gel chromatography and recrystallizing the residue from ethanol, to obtain the captioned compound. Yield 40 mg. m.p. 59.4° C.

The proton NMR data of this compound were as follows:

| σ (ppm) | (TMS internal standard) |
|---|---|
| 8.2–6.9 | (m, 8H) |
| 5.7 | (q, 1H, J=7.4Hz) |
| 4.4 | (q, 2H, J=7.3Hz) |
| 4.0 | (t, 2H, J=6.4Hz) |
| 1.8–0.7 | (m, 18H) |

In the same manner as the above, the following compounds can be prepared:
Ethyl 2-(4'-hexylbiphenylyl-4-carboxyl)-3,3,3-trifluoropropionate
Ethyl 2-(4'-heptylbiphenylyl-4-carboxyl)-3,3,3-trifluoropropionate
Ethyl 2-(4'-octylbiphenylyl-4-carboxyl)-3,3,3-trifluoropropionate
Ethyl 2-(4'-nonylbiphenylyl-4-carboxyl)-3,3,3-trifluoropropionate
Ethyl 2-(4-decylbiphenylyl-4-carboxyl)-3,3,3-trifluoropropionate
Ethyl 2-(4-hexyloxybiphenylyl-4-carboxyl)-3,3,3-trifluoropropionate
Ethyl 2-(4-heptyloxybiphenylyl-4-carboxyl)-3,3,3-trifluoropropionate
Ethyl 2-(4-octyloxybiphenylyl-4-carboxyl)-3,3,3-trifluoropropionate
Ethyl 2-(4-nonyloxybiphenylyl-4-carboxyl)-3,3,3-trifluoropropionate
Ethyl 2-(4-decyloxybiphenylyl-4-carboxyl)-3,3,3-trifluoropropionate
Propyl 2-(4'-hexylbiphenylyl-4-carboxyl)-3,3,3-trifluoropropionate
Propyl 2-(4'-heptylbiphenylyl-4-carboxyl)-3,3,3-trifluoropropionate
Propyl 2-(4'-octylbiphenylyl-4-carboxyl)-3,3,3-trifluoropropionate
Propyl 2-(4'-nonylbiphenylyl-4-carboxyl)-3,3,3-trifluoropropionate
Propyl 2-(4'-decylbiphenylyl-4-carboxyl)-3,3,3-trifluoropropionate
Propyl 2-(4'-hexyloxybiphenylyl-4-carboxyl)-3,3,3-trifluoropropionate
Propyl 2-(4'-heptyloxybiphenylyl-4-carboxyl)-3,3,3-trifluoropropionate
Propyl 2-(4'-octyloxybiphenylyl-4-carboxyl)-3,3,3-trifluoropropionate
Propyl 2-(4'-nonyloxybiphenylyl-4-carboxyl)-3,3,3-trifluoropropionate
Propyl 2-(4'-decyloxybiphenylyl-4-carboxyl)-3,3,3-trifluoropropionate
Butyl 2-(4'-hexylbiphenylyl-4-carboxyl)-3,3,3-trifluoropropionate.
Butyl 2-(4'-heptylbiphenylyl-4-carboxyl)-3,3,3-trifluoropropionate
Butyl 2-(4'-octylbiphenylyl-4-carboxyl)-3,3,3-trifluoropropionate
Butyl 2-(4'-nonylbiphenylyl-4-carboxyl)-3,3,3-trifluoropropionate
Butyl 2-(4'-decylbiphenylyl-4-carboxyl)-3,3,3-trifluoropropionate
Butyl 2-(4'-hexyloxybiphenylyl-4-carboxyl)-3,3,3-trifluoropropionate
Butyl 2-(4'-heptyloxybiphenylyl-4-carboxyl)-3,3,3-trifluoropropionate
Butyl 2-(4'-octyloxybiphenylyl-4-carboxyl)-3,3,3-trifluoropropionate
Butyl 2-(4'-nonyloxybiphenylyl-4-carboxyl)-3,3,3-trifluoropropionate
Butyl 2-(4'-decyloxybiphenylyl-4-carboxyl)-3,3,3-trifluoropropionate
Pentyl 2-(4'-hexylbiphenylyl-4-carboxyl)-3,3,3-trifluoropropionate
Pentyl 2-(4'-heptylbiphenylyl-4-carboxyl)-3,3,3-trifluoropropionate
Pentyl 2-(4'-octylbiphenylyl-4-carboxyl)-3,3,3-trifluoropropionate
Pentyl 2-(4'-nonylbiphenylyl-4-carboxyl)-3,3,3-trifluoropropionate
Pentyl 2-(4'-decylbiphenylyl-4-carboxyl)-3,3,3-trifluoropropionate
Pentyl 2-(4'-hexyloxybiphenylyl-4-carboxyl)-3,3,3-trifluoropropionate
Pentyl 2-(4'-heptyloxybiphenylyl-4-carboxyl)-3,3,3-trifluoropropionate
Pentyl 2-(4'-octyloxybiphenylyl-4-carboxyl)-3,3,3-trifluoropropionate
Pentyl 2-(4'-nonyloxybiphenylyl-4-carboxyl)-3,3,3-trifluoropropionate
Pentyl 2-(4'-decyloxybiphenylyl-4-carboxyl)-3,3,3-trifluoropropionate
Hexyl 2-(4'-hexylbiphenylyl-4-carboxyl)-3,3,3-trifluoropropionate
Hexyl 2-(4'-heptylbiphenylyl-4-carboxyl)-3,3,3-trifluoropropionate
Hexyl 2-(4'-octylbiphenylyl-4-carboxyl)-3,3,3-trifluoropropionate
Hexyl 2-(4'-nonylbiphenylyl-4-carboxyl)-3,3,3-trifluoropropionate
Hexyl 2-(4'-decylbiphenylyl-4-carboxyl)-3,3,3-trifluoropropionate
Hexyl 2-(4'-hexyloxybiphenylyl-4-carboxyl)-3,3,3-trifluoropropionate
Hexyl 2-(4'-heptyloxybiphenylyl-4-carboxyl)-3,3,3-trifluoropropionate
Hexyl 2-(4'-octyloxybiphenylyl-4-carboxyl)-3,3,3-trifluoropropionate
Hexyl 2-(4'-nonyloxybiphenylyl-4-carboxyl)-3,3,3-trifluoropropionate
Hexyl 2-(4'-decyloxybiphenylyl-4-carboxyl)-3,3,3-trifluoropropionate

EXAMPLE 12

Preparation of ethyl 2-(4-(2-(4-hexylphenyl)-pyridine-5-yl)benzoyloxy-3,3,3-trifluoropropionate (compound of the formula (I) wherein $R^1$=hexyl, A=C=phenylene, B=2,5-pyridinylene, v=w=single bond, x=y=—COO— and $R^2$=ethyl)

A mixture of DCC (144.4 mg), DMAP (7.3 mg), methylene chloride (50 ml) and ethyl trifluorolactate obtained in Example 1 (10.0 mg), was stirred at room temperature, followed by dropwise adding a solution of 4-(2-(4-hexylphenyl)pyridine-5-yl)benzoic acid (230 mg) in methylene chloride (25 ml), stirring the mixture for 3 hours, filtering off deposited substance, concentrating the mother liquid, adding toluene (100 ml) to the residue, washing the organic layer with 6N hydrochloric acid, water, 2N NaOH aqueous solution and water in this order, drying over anhydrous sodium sulfate, concentrating and recrystallizing the residue from ethanol, to obtain the captioned compound (150 mg). This compound exhibited chiral smectic phase and its transition points (°C.) were as follows:

Cr 99.5 ScA* 103 Sc* 105.3 SA 141.2 Iso wherein Cr represents crystal, ScA* represents antiferroelectric liquid crystal phase, Sc* represents chiral smectic C phase, SA represents smectic A phase and Iso represents isotropic liquid.

The proton NMR data of this compound were as follows:

| σ (ppm) | (TMS internal standard) |
|---|---|
| 9.0–7.3 | (m, 11H) |
| 5.7 | (q, 1H, J=7.1Hz) |
| 4.4 | (q, 2H, J=7.3Hz) |
| 2.7 | (t, 2H, J=7.6Hz) |
| 1.6–0.7 | (m, 14H) |

In the same manner as the above, the following compounds can be prepared:

Propyl 2-(4-(2-(4-pentylphenyl)-pyridine-5-yl)-benzoyloxy)-3,3,3-trifluoropropionate Propyl 2-(4-(2-(4-hexylphenyl) -pyridine-5-yl)benzoyloxy) -3,3,3-trifluoropropionate Propyl 2-(4-(2-(4-heptylphenyl)-pyridine-5-yl)benzoyloxy) -3,3,3-trifluoropropionate Propyl 2-(4-(2-(4-octylphenyl)-pyridine-5-yl)benzoyloxy)-3,3,3-trifluoropropionate Propyl 2-(4-(2-(4-nonylphenyl)-pyridine-5-yl)benzoyloxy)-3,3,3-trifluoropropionate Butyl 2-(4-(2-(4-pentylphenyl)-pyrimidine-5-yl) benzoyloxy)-3,3,3-trifluoropropionate Butyl 2-(4-(2-(4-hexylphenyl)-pyrimidine-5-yl) benzoyloxy)-3,3,3-trifluoropropionate Butyl 2-(4-(2-(4-heptylphenyl)-pyrimidine-5-yl) benzoyloxy)-3,3,3-trifluoropropionate Butyl 2-(4-(2-(4-octylphenyl)-pyrimidine-5-yl)benzoyloxy) -3,3,3-trifluoropropionate Butyl 2-(4-(2-(4-nonylphenyl)-pyrimidine-5-yl) benzoyloxy)-3,3,3-trifluoropropionate Ethyl 2-(2-(4'-pentylbiphenyl-4-yl)-pyrimidine-5-carboxyl) -3,3,3-trifluoropropionate Ethyl 2-(2-(4'-hexylbiphenyl-4-yl)-pyrimidine-5-carboxyl)-3,3,3-trifluoropropionate Ethyl 2-(2-(4'-heptylbiphenyl-4-yl)-pyrimidine-5-carboxyl) -3,3,3-trifluoropropionate Ethyl 2-(2-(4'-octylbiphenyl-4-yl)-pyrimidine-5-carboxyl)-3,3,3-trifluoropropionate

EXAMPLE 13

Preparation of ethyl 2-(4-(4'-pentyl-4-biphenylcarbonyloxy)benzoyloxy)-3,3,3-trifluoropropionate (compound of the formula (I) wherein $R^1$=octyloxy, A=B=C=1,4-phenylene, v=single bond, w=—COO—, x=—COO—, y=—COO— and $R^2$=ethyl)

First Step

A mixture of 4-benzyloxybenzoic acid chloride (214.4 mg), dry pyridine (5 ml) and ethyl trifluorolactate (100 mg) was stirred at room temperature for 3 hours, followed by adding toluene (100 ml), washing the organic layer with water, 6N hydrochloric acid, water, 2N NaOH aqueous solution and water in this order, drying over anhydrous sodium sulfate, concentrating, purifying the residue according to column chromatography wherein activated alumina was filled and toluene was used as eluent, concentrating the resulting effluent and recrystallizing from ethanol, to obtain ethyl 2-(-(4-benzyloxy)benzoyloxy)-3,3,3-trifluoropropionate (110 mg). m.p. 56.0° C.

Second Step

Ethyl 2-(-(4-benzyloxy )benzoyloxy)-3,3,3-trifluoropropionate obtained at the first step (100 mg), ethyl alcohol (20 ml) and Pd-on-C catalyst (12 mg) were placed in a 50 ml capacity egg-plant type flask to carry out hydrogenolysis, followed by removing the Pd-on-C catalyst, concentrating and recrystallizing the residue from ethyl alcohol, to obtain ethyl 2-(4-hydroxybenzoyloxy)-3,3,3-trifluoropropionate (100 mg). m.p. 83.8° C.

Third Step

A mixture of DCC (61.0 mg), DMAP (7.3 mg), methylene chloride (30 ml), ethyl 2-(4-hydroxybenzoyloxy)-3,3,3-trifluoropropionate (80 mg) and 4'-octyloxy-4-biphenylcarboxylic acid (97 mg) was stirred at room temperature for 4 hours, followed by filtering off deposited substance, concentrating the mother liquid, purifying according to silica gel chromatography and recrystallizing from ethyl alcohol. m.p. of the resulting compound was 67.3° C. This compound exhibited chiral smectic phase and its transition points (°C.) were as follows:

Cr 67.3 ScA* 127.6 SA 155.4 Iso wherein Cr represents crystal, ScA* represents an antiferroelectric liquid crystal phase, Sc* represents chiral smectic c phase, SA represents smectic A phase and Iso represents isotropic liquid.

In the same manner as the above, the following compounds can be prepared:

Propyl 2-(4-(4'-pentyl-4-biphenylcarbonyloxy)benzoyloxy) -3,3,3-trifluoropropionate Propyl 2-(4-(4'-hexyl-4-biphenylcarbonyloxy)benzoyloxy)-3,3,3-trifluoropropionate Propyl 2-(4-(4'-heptyl-4-biphenylcarbonyloxy)benzoyloxy) -3,3,3-trifluoropropionate Propyl 2-(4-(4'-octyl-4-biphenylcarbonyloxy)benzoyloxy)-3,3,3-trifluoropropionate Propyl 2-(4-(4'-nonyl-4-biphenylcarbonyloxy)benzoyloxy)-3,3,3-trifluoropropionate Propyl 2-(4-(4'-decyl-4-biphenylcarbonyloxy)benzoyloxy)-3,3,3-trifluoropropionate Butyl 2-(4-(4-pentyloxy-4-biphenylcarbonyloxy) benzoyloxy)-3,3,3-trifluoropropionate Butyl 2-(4-(4-hexyloxy-4-biphenylcarbonyloxy) benzoyloxy)-3,3,3-trifluoropropionate Butyl 2-(4-(4-heptyloxy-4-biphenylcarbonyloxy) benzoyloxy)-3,3,3-trifluoropropionate Butyl 2-(4-(4-octyloxy-4-biphenylcarbonyloxy) benzoyloxy)-3,3,3-trifluoropropionate Butyl 2-(4-(4-nonyloxy-4-biphenylcarbonyloxy) benzoyloxy)-3,3,3-trifluoropropionate Butyl 2-(4-(4-decyloxy-4-biphenylcarbonyloxy) benzoyloxy)-3,3,3-trifluoropropionate Propyl 2-(4-(4-pentylbenzoyloxy)benzoyloxy)-3,3,3-trifluoropropionate Propyl 2-(4-(4-hexylbenzoyloxy)benzoyloxy)-3,3,3-trifluoropropionate Propyl 2-(4-(4-heptylbenzoyloxy)benzoyloxy)-3,3,3-trifluoropropionate Propyl 2-(4-(4-octylbenzoyloxy)benzoyloxy)-3,3,3-trifluoropropionate Propyl 2-(4-(4-nonylbenzoyloxy)benzoyloxy)-3,3,3-trifluoropropionate Propyl 2-(4-(4-decylbenzoyloxy)benzoyloxy)-3,3,3-trifluoropropionate Pentyl 2-(4-(4-pentyloxybenzoyloxy)benzoyloxy)-3,3,3-trifluoropropionate Pentyl 2-(4-(4-hexyloxybenzoyloxy)benzoyloxy)-3,3,3-trifluoropropionate Pentyl 2-(4-(4-heptyloxybenzoyloxy)benzoyloxy)-3,3,3-trifluoropropionate Pentyl 2-(4-(4-octyloxybenzoyloxy)benzoyloxy)-3,3,3-trifluoropropionate Pentyl 2-(4-(4-nonyloxybenzoyloxy)benzoyloxy)-3,3,3-trifluoropropionate Pentyl 2-(4-(4-decyloxybenzoyloxy)benzoyloxy)-3,3,3-trifluoropropionate Ethyl 2-(4-(4-pentyloxyphenoxycarbonyl)benzoyloxy)-3,3,3-trifluoropropionate Ethyl 2-(4-(4-hexyloxyphenoxycarbonyl)benzoyloxy)-3,3,3-trifluoropropionate Ethyl 2-(4-(4-heptyloxyphenoxycarbonyl)benzoyloxy)-3,3,3-trifluoropropionate Ethyl 2-(4-(4-octyloxyphenoxycarbonyl)benzoyloxy)-3,3,3-trifluoropropionate Ethyl 2-(4-(4-nonyloxyphenoxycarbonyl)benzoyloxy)-3,3,3-trifluoropropionate Ethyl 2-(4-(4-decyloxyphenoxycarbonyl)benzoyloxy)-3,3,3-trifluoropropionate Pentyl 2-(4'-(4-pentyloxybenzoyloxy)-biphenylcarboxy)-3,3,3-trifluoropropionate Pentyl 2-(4'-(4-hexyloxybenzoyloxy)-biphenylcarboxy)-3,3,3-trifluoropropionate Pentyl 2-(4'-(4-heptyloxybenzoyloxy)-biphenylcarboxy)-3,3,3-trifluoropropionate Pentyl 2-(4'-(4-octyloxybenzoyloxy)-biphenylcarboxy)-3,3,3-trifluoropropionate Pentyl 2-(4'-(4-nonyloxybenzoyloxy)-biphenylcarboxy)-3,3,3-trifluoropropionate Pentyl 2-(4'-(4-decyloxybenzoyloxy)-biphenylcarboxy)-3,3,3-trifluoropropionate

EXAMPLE 14

Preparation of 3-(4-nonylphenyl)-6-(2-pentanoyloxy-3,3,3-trifluoropropoxy)-pyridazine (compound of the formula (I) wherein $R^1$=nonyl, A=phenylene, B=3,6-pyridazynylene, C=single bond, v=w=single bond, x=—O—, y=—OCO— and $R^2$=butyl)

First Step

A mixture of sodium hydride (100 mg) with toluene (10 ml) was stirred under ice cooling, followed by gradually dropwise dropping a mixed solution of optically active 2-(2-tetrahydropyranyloxy)-3,3,3-trifluoro-1-propanol obtained in Example 3 (450 mg) with toluene (4 ml), stirring the mixture at room temperature for one hour, pouring a solution of 3-(4-nonylphenyl)-6-chloropyridazine (540 mg) in toluene (10 ml) in the mixture, stirring at 80° C. for 2 hours, extracting the reaction mixture with toluene, washing till the washing liquid became neutral, removing the solvent, purifying according to silica gel chromatography, and drying the residue by a vacuum pump, to obtain 3-(4-nonylphenyl)-6-(2-(2-tetrahydropyranyloxy)-3,3,3-trifluoropropoxy) pyridazine. Yield: 700 mg. m.p. 96.1° C.

The residue was then stirred for one hour together with ehtanol (20 ml) and 3N sulfuric acid aqueous solution (2 ml), followed by cooling the mixture, extracting the solution with ether, washing with water, drying over anhydrous magnesium sulfate, removing the solvent, and drying by means of a vacuum pump, to obtain an optically active 3-(4-nonylphenyl)-6-(2-hydroxy-3,3,3-trifluoropropoxy)-pyridazine (yield: 300 mg).

Second Step

Preparation of the Captioned Compound

A mixture of the pyridazine (100 mg) obtained at the prior step, DCC (60 mg), DMAP (10 mg) and methylene chloride (10 ml) was stirred under ice cooling, followed by dropwise adding a mixed solution of pentanoic acid (30 mg) with methylene chloride (5 ml) to the mixture, stirring for 2 hours, filtering off the deposited solids, concentrating the mother liquid, purifying the residue by means of silica gel column chromatography and recrystallizing the residue from a mixed solvent of ethanol (3):water (2), to obtain the objective optically active 3-(4-nonylphenyl)-6-(2-pentanoyloxy-3,3,3-trifluoropropoxy)-pyridazine. Yield 80 mg. m.p. 43.9° C.

The 1H-NMR chart of this compound is shown in FIG. 2.

In the same manner as the above, the following compounds can be prepared:

3-(4-heptylphenyl)-6-(2-butanoyloxy-3,3,3-trifluoropropoxy)-pyridazine 3-(4-octylphenyl)-6-(2-butanoyloxy-3,3,3-trifluoropropoxy)-pyridazine 3-(4-nonylphenyl)-6-(2-butanoyloxy-3,3,3-trifluoropropoxy)-pyridazine 3-(4-pentyloxyphenyl)-6-(2-butanoyloxy-3,3,3-trifluoropropoxy)-pyridazine 3-(4-hexyloxyphenyl)-6-(2-butanoyloxy-3,3,3-trifluoropropoxy)-pyridazine 3-(4-heptyloxyphenyl)-6-(2-butanoyloxy-3,3,3-trifluoropropoxy)-pyridazine 3-(4-heptylphenyl)-6-(2-pentanoyloxy-3,3,3-trifluoropropoxy)-pyridazine 3-(4-octylphenyl)-6-(2-pentanoyloxy-3,3,3-trifluoropropoxy)-pyridazine 3-(4-pentyloxyphenyl)-6-(2-pentanoyloxy-3,3,3-trifluoropropoxy)-pyridazine 3-(4-hexyloxyphenyl)-6-(2-pentanoyloxy-3,3,3-trifluoropropoxy)-pyridazine 3-(4-heptyloxyphenyl)-6-(2-pentanoyloxy-3,3,3-trifluoropropoxy)-pyridazine 3-(4-heptylphenyl)-6-(2-hexanoyloxy-3,3,3-trifluoropropoxy)-pyridazine 3-(4-octylphenyl)-6-(2-hexanoyloxy-3,3,3-trifluoropropoxy)-pyridazine 3-(4-nonylphenyl)-6-(2-hexanoyloxy-3,3,3-trifluoropropoxy)-pyridazine 3-(4-pentyloxyphenyl)-6-(2-hexanoyloxy-3,3,3-trifluoropropoxy)-pyridazine 3-(4-hexyloxyphenyl)-6-(2-hexanoyloxy-3,3,3-trifluoropropoxy)-pyridazine 3-(4-heptyloxyphenyl)-6-(2-hexanoyloxy-3,3,3-trifluoropropoxy)-pyridazine 3-(4-heptylphenyl)-6-(2-heptanoyloxy-3,3,3-trifluoropropoxy)-pyridazine 3-(4-octylphenyl)-6-(2-heptanoyloxy-3,3,3-trifluoropropoxy)-pyridazine 3-(4-nonylphenyl)-6-(2-heptanoyloxy-3,3,3-trifluoropropoxy)-pyridazine 3-(4-pentyloxyphenyl)-6-(2-heptanoyloxy-3,3,3-trifluoropropoxy)-pyridazine 3-(4-hexyloxyphenyl)-6-(2-heptanoyloxy-3,3,3-trifluoropropoxy)-pyridazine 3-(4-heptyloxyphenyl)-6-(2-heptanoyloxy-3,3,3-trifluoropropoxy)-pyridazine m.p. 41.5° C.

3-(4-heptylphenyl)-6-(2-(2'-butoxy)-propanoyloxy-3,3,3-trifluoropropoxy)-pyridazine 3-(4-octylphenyl)-6-(2-(2'-butoxy)-propanoyloxy-3,3,3-trifluoropropoxy)-pyridazine 3-(4-nonylphenyl)-6-(2-(2'-butoxy)-propanoyloxy-3,3,3-trifluoropropoxy)-pyridazine
(2S, 2'S) form: m.p. 25.5° C.
(2S, 2'R) form: m.p. −7.9° C.

3-(4-pentyloxyphenyl)-6-(2-(2'-butoxy)-propanoyloxy-3,3,3-trifluoropropoxy)-pyridazine 3-(4-hexyloxyphenyl)-6-(2-(2'-butoxy)-propanoyloxy-3,3,3-trifluoropropoxy)-pyridazine 3-(4-heptyloxyphenyl)-6-(2-(2'-butoxy)-propanoyloxy-3,3,3-trifluoropropoxy)-pyridazine
(2S, 2'S) form: m.p. 30.8° C.
(2S, 2'R) form: m.p. 48.3° C.

3-(4-heptylcyclohexylphenyl)-6-(2-heptanoyloxy-3,3,3-trifluoropropoxy)-pyridazine 3-(4-octylcyclohexylphenyl)-6-(2-heptanoyloxy-3,3,3-trifluoropropoxy)-pyridazine 3-(4-nonylcyclohexylphenyl)-6-(2-heptanoyloxy-3,3,3-trifluoropropoxy)-pyridazine 5-(4-hexylphenyl)-2-(2-propanoyloxy-3,3,3-trifluoropropoxy)-pyrimidine 5-(4-heptylphenyl)-2-(2-propanoyloxy-3,3,3-trifluoropropoxy)-pyrimidine 5-(4-octylphenyl)-2-(2-propanoyloxy-3,3,3-trifluoropropoxy)-pyrimidine 5-(4-hexylphenyl)-2-(2-pentanoyloxy-3,3,3-trifluoropropoxy)-pyrimidine 5-(4-heptylphenyl)-2-(2-pentanoyloxy-3,3,3-trifluoropropoxy)-pyrimidine 5-(4-octylphenyl)-2-(2-pentanoyloxy-3,3,3-trifluoropropoxy)-pyrimidine
m.p. 0.6° C.

5-(4-hexylphenyl)-2-(2-(2'-butoxy)-propanoyloxy-3,3,3-trifluoropropoxy)-pyrimidine 5-(4-heptylphenyl)-2-(2-(2'-butoxy)-propanoyloxy-3,3,3-trifluoropropoxy)-pyrimidine 5-(4-octylphenyl)-2-(2-(2'-butoxy)-propanoyloxy-3,3,3-trifluoropropoxy)-pyrimidine
(2S, 2'R) form: m.p. 18.0° C.

EXAMPLE 15

Preparation of Optically Active 2-(4'-pentylbiphenyl-4-yl)-5-(2-pentanoyloxy-3,3,3-trifluoropropoxy)pyrimidine (a compound of the formula (I) wherein $R^1$=pentyl; A=B=phenylene; C=2,5-pyrimidinylene; v=w=single bond; x=—O—; y=—OCO—; and $R^2$=butyl)

First Step

In a flask were placed triphenylphosphine (hereinafter abbreviated to TPP) (1.5 g), 2-(2-(4'-pentylbiphenyl-4-yl)-5-hydroxypyrimidine (0.8 g), 2-(2-tetrahydropyranyloxy)-3,3,3-trifluoro-1-propanol (0.5 g) obtained in Example 3 (0.5 g) and THF (20 ml), followed by dropwise adding a THF (5 ml) solution of diethyl azodicarboxylate (hereinafter abbreviated to DEAD), stirring overnight, distilling off the most part of THF under reduced pressure, extracting the residue with ether, washing with alkali, washing with water, neutralization and purifying by means of silica gel column chromatography, to obtain 2-(4'-pentylbiphenyl-4-yl)-5-(2-(2-tetrapyranyl)oxy-3,3,3-trifluoropropoxy)-pyrimidine (0.4 g).

Second Step 3N-sulfuric acid (10 ml) was added to the total quantity of the above compound, followed by stirring for one hour, extracting the solution with ether, neutralizing, washing with water, concentrating and recrystallizing the residue from hexane, to obtain 2-(4'-pentylbiphenyl-4-yl)-5-(2-hydroxy-3,3,3-trifluoropropoxy)-pyrimidine.

Cr 152.7° C. mesophase 193° C. Iso

Third Step

A mixed solution of 2-(4'-pentylbiphenyl-4-yl)-5-(2-hydroxy-3,3,3-trifluoropropoxy)-pyrimidine (80 mg), pentanoic acid (20 mg), DCC (50 mg), DMAP (10 mg) and methylene chloride (10 ml) was stirred at room temperature, followed by filtering off deposited solids, concentrating the mother liquid, purifying the residue by means of silica gel column chromatography and recrystalizing from ethanol to obtain the objective 2-(4'-pentylbiphenyl-4-yl)-5-(2-pentanoyloxy-3,3,3-trifluoropropoxy)-pyrimidine (90 mg).

Cr 33° C. mesophase 84° C. iso

In the same manner as the above, the following compounds can be prepared:

2-(4'-pentylbiphenyl-4-yl)-5-(2-butanoyloxy-3,3,3-trifluoropropoxy)-pyrimidine 2-(4'-hexylbiphenyl-4-yl)-5-(2-butanoyloxy-3,3,3-trifluoropropoxy)-pyrimidine 2-(4'-heptylbiphenyl-4-yl)-5-(2-butanoyloxy-3,3,3-trifluoropropoxy)-pyrimidine 2-(4'-pentylbiphenyl-4-yl)-5-(2-(2'-butoxypropanoyloxy)-3,3,3-trifluoropropoxy)-pyrimidine
(2S, 2'S) form: m.p. 72.1° C.
(2S, 2'R) form: Cr 54.9 SA 77.7 Iso 2-(4'-hexylbiphenyl-4-yl)-5-(2-(2'-butoxypropanoyloxy)-3,3,3-trifluoropropoxy)-pyrimidine 2-(4'-heptylbiphenyl-4-yl)-5-(2-(2'-butoxypropanoyloxy)-3,3,3-trifluoropropoxy)-pyrimidine 1-pentanoyloxy-2-(3-fluoro-4-(5-hexylpyrimidine-2-yl)phenoxy)-3,3,3-trifluoropropane 1-pentanoyloxy-2-(3-fluoro-4-(5-heptylpyrimidine-2-yl)phenoxy)-3,3,3-trifluoropropane 1-pentanoyloxy-2-(3-fluoro-4-(5-octylpyrimidine-2-yl)phenoxy)-3,3,3-trifluoropropane
m.p. 5.3° C.

1-pentanoyloxy-2-(3-fluoro-4-(5-nonylpyrimidine-2-yl)phenoxy)-3,3,3-trifluoropropane 1-butanoyloxy-2-(3-fluoro-4-(5-hexylpyrimidine-2-yl)phenoxy)-3,3,3-trifluoropropane 1-butanoyloxy-2-(3-fluoro-4-(5-heptylpyrimidine-2-yl)phenoxy)-3,3,3-trifluoropropane 1-butanoyloxy-2-(3-fluoro-4-(5-octylpyrimidine-2-yl)phenoxy)-3,3,3-trifluoropropane 1-butanoyl)-2-(3-fluoro-4-(5-nonylpyrimidine-2-yl)-phenoxy)-3,3,3-trifluoropropane 2-(4-octyloxyphenyl)-5-(2-(2'-propoxypropanoyloxy)-3,3,3-trifluoropropoxy)-pyrimidine 2-(4-octyloxyphenyl)-5-(2-(2'-butoxypropanoyloxy)-3,3,3-trifluoropropoxy)-pyrimidine
m.p. 29.8° C.

2-(4-octyloxyphenyl)-5-(2-(2'-pentyloxypropanoyloxy)-3,3,3-trifluoropropoxy)-pyrimidine 2-(4-octyloxyphenyl)-5-(2-(2'-hexyloxypropanoyloxy)-3,3,3-trifluoropropoxy)-pyrimidine 1-butanoyloxy-2-(4-(5-hexylpyridine-2-yl)phenoxy)-3,3,3-trifluoropropane 1-butanoyloxy-2-(4-(5-heptylpyridine-2-yl)phenoxy)-3,3,3-trifluoropropane 1-butanoyloxy-2-(4-(5-octylpyridine-2-yl)phenoxy)-3,3,3-trifluoropropane 1-butanoyloxy-2-(4-(5-nonylpyridine-2-yl)phenoxy)-3,3,3-trifluoropropane

EXAMPLE 16

A mixture of 2-(4'-pentylbiphenyl-4-yl)-5-(2-hydroxy-3,3,3-trifluoropropoxy)-pyrimidine (60 mg), pentyl iodide (30 mg) and silver oxide (40 mg) was stirred overnight, followed by filtering off insoluble substance, concentrating the mother liquid and recrystallizing from ethanol to obtain 2-(4'-pentylbiphenyl-4-yl)-5-(2-pentyloxy-3,3,3-trifluoropropoxy)-pyrimidine (30 mg).

Cr 11 N* 52.7 Iso

In the same manner as the above, the following compounds can be prepared:

2-(4'-pentylbiphenyl-4-yl)-5-(2-butoxy-3,3,3-trifluoropropoxy)-pyrimidine
2-(4'-pentylbiphenyl-4-yl)-5-(2-hexyloxy-3,3,3-trifluoropropoxy)-pyrimidine
2-(4'-pentylbiphenyl-4-yl)-5-(2-heptyloxy-3,3,3-trifluoropropoxy)-pyrimidine
2-(4'-heptylbiphenyl-4-yl)-5-(2-pentyloxy-3,3,3-trifluoropropoxy)-pyrimidine
2-(4'-octylbiphenyl-4-yl)-5-(2-pentyloxy-3,3,3-trifluoropropoxy)-pyrimidine
1-(4'-(5-butylpyridine-2-yl)-4-biphenylyloxy)-2-butoxy-3,3,3-trifluoropropane
1-(4'-(5-pentylpyridine-2-yl)-4-biphenylyloxy)-2-butoxy-3,3,3-trifluoropropane
1-(4'-(5-hexylpyridine-2-yl)-4-biphenylyloxy)-2-butoxy-3,3,3-trifluoropropane
1-(4'-(5-heptylpyridine-2-yl)-4-biphenylyloxy)-2-butoxy-3,3,3-trifluoropropane
1-(4-(5-hexylpyrimidine-2-yl)phenoxy)-2-butoxy-3,3,3-trifluoropropane

EXAMPLE 17

Using (–)-2-butoxy-3,3,3-trifluoro-1-propanol prepared in Example 8, TPP, DEAD and 5-hexyl-2-(4-hydroxyphenyl)pyrimidine, it is possible to prepare 1-(4-(5-hexylpyrimidine-2-yl)phenoxy)-2-butoxy-3,3,3-trifluoropropane.

In the same manner as the above, the following compounds can be prepared:

1-(4-(5-hexylpyrimidine-2-yl)phenoxy)-2-butoxy-3,3,3-trifluoropropane
1-(4-(5-hexylpyrimidine-2-yl)phenoxy)-2-pentyloxy-3,3,3-trifluoropropane
1-(4-(5-hexylpyrimidine-2-yl)phenoxy)-2-hexyloxy-3,3,3-trifluoropropane
1-(4-(5-hexylpyrimidine-2-yl)phenoxy)-2-heptyloxy-3,3,3-trifluoropropane
1-(4-(5-octylpyridine-2-yl)phenoxy)-2-butoxy-3,3,3-trifluoropropane
1-(4-(5-octylpyridine-2-yl)phenoxy)-2-pentyloxy-3,3,3-trifluoropropane
1-(4-(5-octylpyridine-2-yl)phenoxy)-2-hexyloxy-3,3,3-trifluoropropane
1-(4-(5-octylpyridine-2-yl)phenoxy)-2-heptyloxy-3,3,3-trifluoropropane
1-(4-(2-nonyloxypyrimidine-5-yl)phenoxy)-2-butoxy-3,3,3-trifluoropropane
1-(4-(2-nonyloxypyrimidine-5-yl)phenoxy)-2-pentyloxy-3,3,3-trifluoropropane
1-(4-(2-nonyloxypyrimidine-5-yl)phenoxy)-2-hexyloxy-3,3,3-trifluoropropane
1-(4-(2-nonyloxypyrimidine-5-yl)phenoxy-2-heptyloxy-3,3,3-trifluoropropane
1-(2-(4-octyloxyphenyl)pyrimidine-5-oxy)-2-butoxy-3,3,3-trifluoropropane
1-(2-(4-octyloxyphenyl)pyrimidine-5-oxy)-2-pentyloxy-3,3,3-trifluoropropane
1-(2-(4-octyloxyphenyl)pyrimidine-5-oxy)-2-hexyloxy-3,3,3-trifluoropropane
1-(2-(4-octyloxyphenyl)pyrimidine-5-oxy)-2-heptyloxy-3,3,3-trifluoropropane
1-(4-(2-(4-nonylphenyl)pyrimidine-5-yl)phenoxy)-2-butoxy-3,3,3-trifluoropropane
1-(4-(2-(4-nonylphenyl)pyrimidine-5-yl)phenoxy)-2-pentyloxy-3,3,3-trifluoropropane
1-(4-(2-(4-nonylphenyl)pyrimidine-5-yl)phenoxy)-2-(2-methylbutoxy)-3,3,3-trifluoropropane
1-(4-(2-(4-nonylphenyl)pyrimidine-5-yl)phenoxy)-2-hexyloxy-3,3,3-trifluoropropane
1-(4-(2-(4-nonylphenyl)pyrimidine-5-yl)phenoxy)-2-heptyloxy-3,3,3-trifluoropropane

EXAMPLE 18

Preparation of 4-(2-(4-hexylphenyl)-pyridine-5-yl) phenyl 2-pentyloxy-3,3,3-trifluoropropionate (a compound of thr formula (I) wherein $R^1$=hexyl; A=C=phenylene; B=2,5-pyridinylene, v=w=single bond; x=—OCO—; y=—O—; and $R^2$=pentyl)

A mixed solution of (–)-2-pentyloxy-3,3,3-trifluoropropionic acid obtained in Example 6 (100 mg), 4-(5-(4-octylphenyl)-pyridine-2-yl)phenol (160 mg), DCC (100 mg), DMAP (10 mg) and methylene chloride (10 ml) was stirred at room temperature, followed by filtering off deposited solids, concentrating the mother liquid, purifying the residue by means of silica gel column chromatography and recrystallizing the residue from ethanol. yield: 140 mg.

Cr 88 Sc* 103.7 SA 132.7 Iso

In the same manner as the above, the following compounds can be prepared:

4-(2-(4-butylphenyl)-pyridine-5-yl)phenyl 2-propoxy-3,3,3-trifluoropropionate
4-(2-(4-pentylphenyl)-pyridine-5-yl)phenyl 2-propoxy-3,3,3-trifluoropropionate
4-(2-(4-hexylphenyl)-pyridine-5-yl)phenyl 2-propoxy-3,3,3-trifluoropropionate
4-(2-(4-heptylphenyl)-pyridine-5-yl)phenyl 2-propoxy-3,3,3-trifluoropropionate
4-(2-(4-octylphenyl)-pyridine-5-yl)phenyl 2-propoxy-3,3,3-trifluoropropionate
4-(2-(4-nonylphenyl)-pyridine-5-yl)phenyl 2-propoxy-3,3,3-trifluoropropionate
4-(2-(4-butyloxyphenyl)-pyridine-5-yl)phenyl 2-butoxy-3,3,3-trifluoropropionate
4-(2-(4-pentyloxyphenyl)-pyridine-5-yl)phenyl 2-butoxy-3,3,3-trifluoropropionate
4-(2-(4-hexyloxyphenyl)-pyridine-5-yl)phenyl 2-butoxy-3,3,3-trifluoropropionate
4-(2-(.4-heptyloxyphenyl)-pyridine-5-yl)phenyl 2-butoxy-3,3,3-trifluoropropionate
4-(2-(4-octyloxyphenyl)-pyridine-5-yl) phenyl 2-butoxy-3,3,3-trifluoropropionate
4-(2-(4-nonyloxyphenyl)-pyridine-5-yl)phenyl 2-butoxy-3,3,3-trifluoropropionate
4-(5-(4-butylphenyl)-pyridine-2-yl) phenyl 2-pentyloxy-3,3,3-trifluoropropionate Room temperature SA 177.1 Iso 4-(5-(4-pentylphenyl)-pyridine-2-yl)phenyl 2-pentyloxy-3,3,3-trifluoropropionate 4-(5-(4-hexylphenyl)-pyridine-2-yl) phenyl 2-pentyloxy-3,3,3-trifluoropropionate
4-(5-(4-heptylphenyl)-pyridine-2-yl) phenyl 2-pentyloxy-3,3,3-trifluoropropionate
4-(5-(4-octylphenyl)-pyridine-2-yl)phenyl 2-pentyloxy-3,3,3-trifluoropropionate
4-(5-(4-nonylphenyl)-pyridine-2-yl) phenyl 2-pentyloxy-3,3,3-trifluoropropionate
3-fluoro-4-(2-(4-butylphenyl)-pyridine-5-yl) phenyl 2-pentyloxy-3,3,3-trifluoropropionate Cr 102.1 SA 145.2 Iso 3-fluoro-4-(2-(4-pentylphenyl)-pyridine-5-yl) phenyl 2-pentyloxy-3,3,3-trifluoropropionate
3-fluoro-4-(2-(4-hexylphenyl)-pyridine-5-yl)phenyl 2-pentyloxy-3,3,3-trifluoropropionate
3-fluoro-4-(2-(4-heptylphenyl)-pyridine-5-yl) phenyl 2-pentyloxy-3,3,3-trifluoropropionate
3-fluoro-4-(2-(4-octylphenyl)-pyridine-5-yl) phenyl 2-pentyloxy-3,3,3-trifluoropropionate
3-fluoro-4-(2-(4-nonylphenyl)-pyridine-5-yl) phenyl 2-pentyloxy-3,3,3-trifluoropropionate
4-(2-(4-butylphenyl)-pyrimidine-5-yl)phenyl 2-pentyloxy-3,3,3-trifluoropropionate
4-(2-(4-pentylphenyl)-pyrimidine-5-yl) phenyl 2-pentyloxy-3,3,3-trifluoropropionate
4-(2-(4-hexylphenyl)-pyrimidine-5-yl) phenyl 2-pentyloxy-3,3,3-trifluoropropionate
4-(2-(4-heptylphenyl)-pyrimidine-5-yl) phenyl 2-pentyloxy-3,3,3-trifluoropropionate
4-(2-(4-octylphenyl)-pyrimidine-5-yl) phenyl 2-pentyloxy-3,3,3-trifluoropropionate
4-(2-(4-nonylphenyl)-pyrimidine-5-yl) phenyl 2-pentyloxy-3,3,3-trifluoropropionate
m.p. 121.6° C.
2-(4'-butylbiphenyl-4-yl)-pyrimidine-5-yl 2-pentyloxy-3,3,3-trifluoropropionate
2-(4'-pentylbiphenyl-4-yl)-pyrimidine-5-yl 2-pentyloxy-3,3,3-trifluoropropionate Cr 105 (S 94.1) SA 115.4 Iso 2-(4'-hexylbiphenyl-4-yl)-pyrimidine-5-yl 2-pentyloxy-3,3,3-trifluoropropionate
2-(4'-heptylbiphenyl-4-yl)-pyrimidine-5-yl 2-pentyloxy-3,3,3-trifluoropropionate
2-(4'-butylbiphenyl-4-yl)-pyrimidine-5-yl 2-hexyloxy-3,3,3-trifluoropropionate
2-(4'-pentylbiphenyl-4-yl)-pyrimidine-5-yl 2-hexyloxy-3,3,3-trifluoropropionate
2-(4'-hexylbiphenyl-4-yl)-pyrimidine-5-yl 2-hexyloxy-3,3,3-trifluoropropionate
2-(4'-heptylbiphenyl-4-yl)-pyrimidine-5-yl 2-hexyloxy-3,3,3-trifluoropropionate
4'-pentylbiphenyl-4-yl 2-heptyloxy-3,3,3-trifluoropropionate
4'-hexylbiphenyl-4-yl 2-heptyloxy-3,3,3-trifluoropropionate
4'-heptylbiphenyl-4-yl 2-heptyloxy-3,3,3-trifluoropropionate
4'-octylbiphenyl-4-yl 2-heptyloxy-3,3,3-trifluoropropionate
4'-nonylbiphenyl-4-yl 2-heptyloxy-3,3,3-trifluoropropionate
4'-pentyloxybiphenyl-4-yl 2-pentyloxy-3,3,3-trifluoropropionate
4'-hexyloxybiphenyl-4-yl 2-pentyloxy-3,3,3-trifluoropropionate
4'-pentyloxybiphenyl-4-yl 2-pentyloxy-3,3,3-trifluoropropionate
4'-octyloxybiphenyl-4-yl 2-pentyloxy-3,3,3-trifluoropropionate
m.p. 78.6° C.
4'-nonyloxybiphenyl-4-yl 2-pentyloxy-3,3,3-trifluoropropionate EXAMPLE 19 (Measurement Example 1)

The spontaneous polarization and tilt angle of a single compound 2-(4-(2-(4-hexylphenyl)-pyridine-5-yl)-benzoyloxy)-3,3,3-trifluoropropionate exhibiting a ferroelectric liquid crystal phase by itself were measured.

| Tc - T | 5 | 10 | 15 | 20 | 30 |
|---|---|---|---|---|---|
| Spontaneous polarization | 96.8 | 116.6 | 138.8 | 151.0 | 158.1 |
| Tilt angle | 26.4 | 30.1 | 34.1 | 34.7 | 35.6 |

EXAMPLE 20 (Use Example 1)

| | |
|---|---|
| 5-Octyl-2-(4-hexyloxyphenyl)pyrimidine | 30 wt. % |
| 5-Octyl-2-(4-octyloxyphenyl)pyrimidine | 20 wt. % |
| 5-Octyl-2-(4-nonyloxyphenyl)pyrimidine | 10 wt. % |
| 5-Octyl-2-(4-decyloxyphenyl)pyrimidine | 10 wt. % |
| 5-Octyl-2-(4'-pentyl-4-biphenylyl)pyrimidine | 20 wt. % |
| 5-Octyl-2-(4'-heptyl-4-biphenylyl)pyrimidine | 10 wt. % |

The liquid crystal composition (A) of the above composition exhibits the following phase transition points (°C.):

Cr 4 Sc 65 SA 79 N 90 Iso wherein Cr, Sc, SA, N and Iso respectively represent crystal, smectic C phase, smectic A phase, nematic phase and isotropic liquid.

A composition (B) consisting of the above composition (A) (90 wt. %) and optically active 3-(4-nonylphenyl)-6-(2-pentanoyloxy-3,3,3-trifluoropropoxy)pyridazine (10 wt. %) exhibited the following phase transition points:

Sc -44.4 SA 74.2 N 84.7 Iso

Use Reference Example 1

A mixture (composition C) of the above composition (A) (90 wt. %) with 3-(4-nonylphenyl)-6-(2-pentanoyloxypropoxy)pyridazine (10 wt. %) exhibited the following phase transition points:

Sc 53.3 SA 67.3 N 71.9 Iso wherein Sc, SA, N and Iso are as defined above.

In order to clarify the superiority of the composition (B) using the compound of the present invention, comparison of the physical properties at 40° C. of the ferroelectric liquid crystal of the composition (B) with those of the composition (C) is shown in Table 1.

TABLE 1

Comparison of the physical properties of the composition (B) with those of composition (C)

| | PS (nC/cm²) | Po (nC/cm²) | τ (μsec) | ηo (mPaμsec) | θ (°) |
|---|---|---|---|---|---|
| Composition B | 5.9 | 27.9 | 14 | 42.5 | 12 |
| Composition C | 0.9 | 3.8 | 70 | 38.7 | 13 |

EXAMPLE 21 (Use Example 2)

| 4'-ethyl-4-cyanobiphenyl | 20 wt. % |
|---|---|
| 4'-pentyl-4-cyanobiphenyl | 35 wt. % |
| 4'-octyl-4-cyanobiphenyl | 30 wt. % and |
| 4'-pentyl-4-cyanobiphenyl | 15 wt. % | was poured into a cell provided with transparent electrodes each obtained by coating polyvinyl alcohol on the surface for aligning treatment, followed by rubbing the resulting surface for parallel treatment, the distance between the electrodes being 10 μm, to prepare a TN mode display cell. This cell was observed using a polarizing microscope. As a result, it was observed that reverse domain occurred. To this nematic liquid crystal composition was added optically active 1,1,1-trifluoro-3-ethoxy-2-propyl 4-(4-octyloxyphenyl)benzoate as a compound of the present invention (0.1 wt. %), followed by preparing the same TN mode cell as the above and observing it. As a result, a uniform nematic phase was observed without occurrence of reverse domain.

EXAMPLE 22 (Use Example 3)

To ZLI-1132 made by Merck Co., Ltd. was 2-(4-(2-(4-hexylphenyl)-pyridine-5-yl)-benzoyloxy)-3,3,3-trifluoropropionate (1 wt. %). The chiral nematic liquid crystal composition has the following chiral pitch lengths:

| Temperature (°C.) | Pitch length (μm) |
|---|---|
| 20 | 8.1 |
| 30 | 8.2 |
| 40 | 8.4 |
| 50 | 8.6 |
| 60 | 8.8 |

As shown above, the nematic chiral pitch length induced by the compound of the present invention is so short that it is optimum to the display mode requiring a high twisted force for STN, etc.

Further, the above pitch length does not depend upon temperature so much. In other words, it exhibits a flat change relative to the temperature. This suggests a possibility of realizing a display element requiring no temperature compensation, etc.

Commercial Utilizability:

The first of the specific properties of the compound of the present invention consists in that its spontaneous polarization value is very large, in some cases, due to the structure of the optically active part of the present invention. A compound exhibiting a ferroelectric liquid crystal phase by itself has a very large spontaneous polarization value. For example, as described later in Example 4, there is a compound exhibiting a spontaneous polarization value of 150 nC/cm² or more. Even in the case of a compound exhibiting no ferroelectric liquid crystal phase by itself, when it is added to an achiral basic substance described above, a ferroelectricity is induced and its spontaneous polarization value is very large. For example, as described later in detail in Example 6, a sufficient ferroelectricity is induced by adding the compound of the present invention and a composition endurable to practical use can be constituted. This fact means that the compound of the present invention has a potentially very large spontaneous polarization value irrespective of whether or not the compound exhibits a ferroelectric liquid crystal phase. As already described, a large spontaneous polarization value is connected to shortening of response time, and shows a possibility of realizing a moving image display element.

A compound exhibiting a ferroelectric liquid crystal phase by itself has a very large spontaneous polarization value. Even in the case of a compound exhibiting no ferroelectric liquid crystal, when it is added to the above-described achiral basic substance, a ferroelectricity is induced, and its spontaneous polarization value is far larger than those obtained so far. For example, as a compound having an optically active site, derived from conventional optically active lactic acid esters, the following compound is known

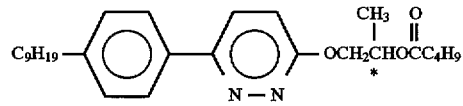

In order to clarify the specific features of the compound of the present invention derived from an optically active trifluorolactic acid ester, the various physical properties of a composition obtained by adding the compound of the present invention (compound of Example 1) (10 wt. %) derived from an optically active trifluorolactic acid ester to an achiral basic substance and those of a composition obtained by adding the above compound (VI) (10 wt. %) derived from a conventional optically active lactic acid ester to the achiral basic substance are shown in Table 1 (see Table 1 of Example 20).

As apparent from Table 1, the ferroelectric liquid crystal composition (composition (B)) using a compound of the present invention derived from an optically active trifluorolactic acid ester has a spontaneous polarization value of 6 times or more that of the composition (composition (C)) using a compound (VI) derived from a conventional optically active lactic acid ester (the value further notably increases in the case of specified Po, that is, the value reaches 7 times or more). Further, it is seen that so far developed ferroelectric liquid crystals have raised a drawback that the larger the spontaneous polarization value, the higher the viscosity, whereas in the case of the compound of the present invention, the viscosity almost does not increase in spite of increase of its spontaneous polarization value with a leap. As a result, the response speed is also made higher with a leap as high as five times the conventional one.

Thus, it can be said that a possibility of realizing a moving image display element using a ferroelectric liquid crystal has been notably increased. A similar tendency is also observed in the case of the compounds of Examples 10 and 11; hence the above tendency can be regarded as a general tendency of the compound of the present invention.

Further, the second of the specific features of the compound of the present invention consists in that some of the compounds of the present invention exhibit an antiferroelectric liquid crystal phase (see Japanese Journal of Applied Physics, 28, (1989), p. 1265).

A display mode utilizing the switching between this antiferroelectric liquid crystal phase and a ferroelectric liquid crystal phase has been proposed. The specific features of this display element consist in a high resolution, a high contrast, etc., and the realizations thereof have been expected. For the first of the realization, a liquid crystal material exhibiting an antiferroelectric liquid crystal phase within a broad range from low temperature to high temperature is required. However, few compounds exhibiting the antiferroelectric liquid crystal phase have been known till now.

Some of the compounds of the present invention exhibit the antiferroelectric liquid crystal phase within a broad range from low temperature to high temperature, and the temperature range exhibiting the antiferroelectric liquid crystal phase is far broader than those of so far known compounds. For example, a compound (MHPOBC) having been found to exhibit the antiferroelectric liquid crystal phase and yet having been known as a representative compound at present, exhibits the following structure and transition points:

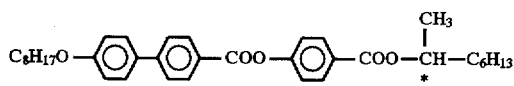

Cr 30 SIA* 66 ScA* 118.3 Scγ* 119 Scβ* 120.7 Scα* 122 SA 156 Iso wherein Scα* represents an intermediate phase between SA phase and Sc* phase, Scβ* represents Sc* phase, an intermediate phase between Scγ* C* phase and ScA* phase and SIA* phase represents an antiferroelectric liquid crystal phase having a higher order than that of ScA*. Iso, SA, ScA* and Cr are as defined above, and SIA* 30 Cr represents a recrystallization temperature (see Japanese Journal of Applied Physics, 29, No. 6, June, 1990, 1122–1127).

The antiferroelectric liquid crystal phase having been utilized at present is the one utilizing ScA* phase. Thus, it is preferred that a higher order phase other than ScA* phase be absent in the compound added to the composition. As described below in Example, the compound of Example 2 having a structure similar to that of MHPOBC is deficient in a higher order antiferroelectric liquid crystal phase as seen in MHPOBC. And yet, it is seen that the exhibited antiferroelectric liquid crystal phase is only ScA* phase and its temperature range is very broad.

Further, as an antiferroelectric liquid crystal material having trifluoromethyl group, there is a compound of TFM-HPOBC. Its structure and phase transition points are as follows:

Cr 60.1 ScA* 108.0 Sc* 109.0 SA 121.0 Iso (see 15th Liquid Crystal Forum, 3A17).

As described below in detail in Example 2, it is seen that the upper limit temperature of the compound of the present invention (compound of Example 2) is higher by about 20° C. than that of TFMHPOBC. This characteristic can be said to be important when an antiferroelectric liquid crystal composition is constituted.

As described above, when the compound of the present invention is utilized as an antiferroelectric liquid crystal, the temperature range exhibiting an antiferroelectric liquid crystal phase is broad and yet a higher order antiferroelectric liquid crystal phase is not exhibited; hence the compound can be suitably utilized for the above-mentioned display mode.

Further, the third of the specific features of the compound of the present invention having derived an optically active trifluorolactic acid ester consists in that the optically active lactic acid ester derivative has a far lower melting point than those of conventional optically active lactic acid ester derivatives. Among the compounds, there is a compound exhibiting a melting point lower than ice-cooled temperature or lower, as low as –7.9° C. When a similar composition was prepared using a conventional optically active lactic acid ester derivative (VI) and the response speed at 25° C. was measured, the composition crystallized; thus the measurement was impossible. As the cause, it is considered that since the melting point of (VI) is as high as 87° C., the melting point of the composition itself has been raised. Whereas, the melting point of the compound of the present invention (compound of Example 1) which is a trifluoro analogue of (VI) was 43.9° C., that is, about a half of that of (VI). Further, even when similar compositions were prepared, no crystallization occurred at 25° C., the response speed could be measured and high speed response properties as high as 27 μsec were exhibited. Namely, the ferroelectric liquid crystal composition using the compound of the present invention has a melting point not so high as those of conventional compositions; hence there is a possibility of broadening the temperature range of ferroelectric liquid crystals down to low temperatures.

What we claim is:

1. An optically active compound expressed by the formula (I)

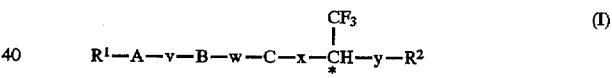

wherein $R^1$ represents either one of an alkyl group, or alkoxy group of 1 to 18 carbon atoms, or an alkanoyl group, alkanoyloxy group or alkoxycarbonyl group of 2 to 18 carbon atoms, $R^2$ represents an alkyl group which may be substituted by an alkoxy group (the total of the carbon atoms being 1 to 15), A, B and C each independently are selected from the group consisting of

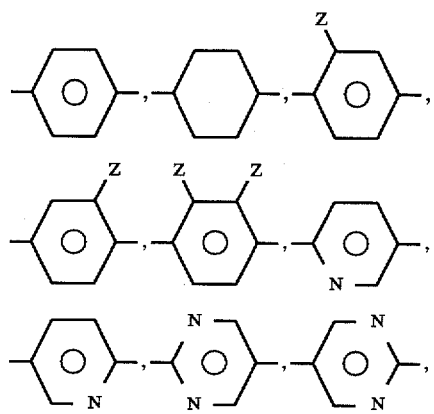

-continued

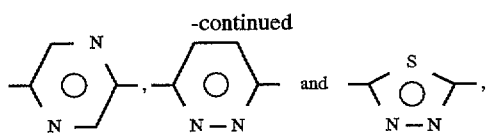

or C represents a single bond when w defined below represents a single bond, Z represents a chlorine atom or a fluorine atom, v and w each independently are selected from the group consisting of —COO—, —OCO—, —CH$_2$O—, —OCH$_2$—, —CH$_2$CH$_2$—, —CH=CH—, —C≡C— and a single bond, and x and y each are respectively selected from the following combinations consisting of —COO— and —COO—, —COO— and —CO—, —COO— and —CH$_2$O—, —COO— and —CH$_2$OCO—, —COO— and —CH$_2$OCOO—, —O— and —CH$_2$O—, —O— and —CH$_2$OCO—, —O— and —CH$_2$OCOO—.

2. A liquid crystal composition comprising at least one kind of the compound as set forth in claim 1.

3. A liquid crystal composition wherein the liquid crystal phase exhibited in claim 2 is a chiral smectic phase.

4. A liquid crystal composition wherein the liquid crystal phase exhibited in claim 2 is a chiral nematic phase.

5. A light-switching element constituted by using a liquid crystal composition comprising at least one kind of the compound as set forth in claim 1.

6. An optically active compound expressed by the formula

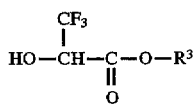

wherein R$^3$ represents an alkyl group or aralkyl group of 1 to 10 carbon atoms.

7. An optically active compound used for a component of a liquid crystal composition and expressed by the formula

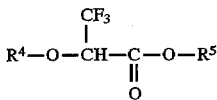

wherein R$^4$ represents an alkyl group, alkanoyl group or alkoxycarbonyl group of 1 to 16 carbon atoms, each of which may be substituted by an alkoxy group, and R$^5$ represents a hydrogen atom, an alkyl group or aralkyl group of 1 to 10 carbon atoms.

8. An optically active compound expressed by the formula

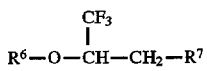

wherein R$^5$ represents an alkyl group or aralkyl group of 1 to 16 carbon atoms each of which may be substituted by an alkoxy group, and R$^7$ represents a hydroxyl group, a halogen atom, methanesulfonyloxy group, p-toluenesulfonyloxy group or benzenesulfonyloxy group.

9. An optically active compound expressed by the formula

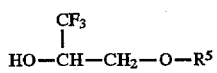

wherein R$^5$ represents hydrogen atom or an alkyl group or aralkyl group of 1 to 5 carbon atoms.

* * * * *